(12) United States Patent
Taverna et al.

(10) Patent No.: US 9,606,113 B2
(45) Date of Patent: Mar. 28, 2017

(54) METHOD FOR DIAGNOSING ALZHEIMER'S DISEASE

(71) Applicants: CENTRE NATIONAL DE LA RECHERCHE SCIENTIFIQUE (C.N.R.S), Paris (FR); Universite Paris-Sud 11, Orsay (FR)

(72) Inventors: Myriam Taverna, Sceaux (FR); Romain Verpillot, Paris (FR); Markus Otto, Ulm (DE); Hans Klafki, Essen (DE)

(73) Assignees: Centre National De La Recherche Scientifique (C.N.R.S) (FR); Universite Paris-Sud 11 (FR)

( * ) Notice: Subject to any disclaimer, the term of this patent is extended or adjusted under 35 U.S.C. 154(b) by 0 days.

(21) Appl. No.: 14/345,179

(22) PCT Filed: Sep. 17, 2012

(86) PCT No.: PCT/EP2012/068268
§ 371 (c)(1),
(2) Date: Mar. 14, 2014

(87) PCT Pub. No.: WO2013/038014
PCT Pub. Date: Mar. 21, 2013

(65) Prior Publication Data
US 2014/0370529 A1    Dec. 18, 2014

(30) Foreign Application Priority Data

Sep. 16, 2011 (EP) .................................. 11306171

(51) Int. Cl.
*G01N 33/543*     (2006.01)
*G01N 33/68*      (2006.01)

(52) U.S. Cl.
CPC ... *G01N 33/54306* (2013.01); *G01N 33/6896* (2013.01); *G01N 2800/2821* (2013.01); *G01N 2800/52* (2013.01)

(58) Field of Classification Search
None
See application file for complete search history.

(56) References Cited

U.S. PATENT DOCUMENTS

| 4,511,659 A | 4/1985 | Matson |
| 4,812,362 A * | 3/1989 | Stolowitz ............... B01J 20/281 428/407 |
| 2011/0097736 A1* | 4/2011 | Fonteh et al. ................. 435/7.4 |

(Continued)

FOREIGN PATENT DOCUMENTS

EP       0371517 A1    6/1990

OTHER PUBLICATIONS

Hsieh 2005 "Discontinous electrolyte systems for improved detection of biologically active amines and acids by capillary electrophoresis with laser-induced native fluorescence detection" Electrophoresis 26:187-195.*

(Continued)

*Primary Examiner* — Adam M Weidner
(74) *Attorney, Agent, or Firm* — Polster Lieder

(57) ABSTRACT

The present invention relates to a method for diagnosing a neurodegenerative disease in a subject, wherein the level of each of at least two catecholamines is measured in a sample of biological fluid from said subject.

6 Claims, 9 Drawing Sheets

(56) References Cited

U.S. PATENT DOCUMENTS

2011/0207228 A1* 8/2011 Sohn .................. C07D 249/04
436/17

OTHER PUBLICATIONS

McKhann 1984 "clinical diagnosis of alzheimer's disease" Neurology 34:939.*
Robert 1995 "capillary zone electrophoresis with laser-induced fluorescence detection for the determination of nanomolar concentrations of noradrenaline and dopamine: application to brain microdialysate analysis" analytical chem 67(11):1838-1844.*
Zhou 2008 "nonaqueous capillary electrophoresis with laser-induced fluorescence detection: a case study of comparison with aqueous media" analytica chimica acta 611:212-219.*
Dictionary.com 2015 "Exclusive" accessed from dictionary.reference.com on Dec. 3, 2015.*
ATDBio 2016 "Alexa Dyes" accessed from atdbio.com.*
SciFinder 2016 "CAS Registry No. 247144-99-6" accessed from scifinder.cas.org.*
ThermoFisher 2016 "Alexa Fluor 488 Protein labeling kit" accessed from thermofisher.com.*
Vial 2008 "PAI1 stimulates assembly of the fibronectin matrix in osterosrcoma cells through crosstalk between the .alpha.v.beta.5 and .alpha.5.beta.1 integrins" J cell science 121(10): 1661-1670.*
Yoshitake 2004 "determination of serotonin, noradrenaline, dopamine and their metabolites in rat brain extracts and microdialysis samples by column liquid chromatography with fluorescence detection following derivatization with benzylamine and 1,2-diphenylethylenediamine" J chromatography 807:177-183.*
Coppi 2002 "the enteric parasite entamoeba uses an autocrine catecholamine system during differentiation into the infectious cyst stage" JBC 277(10):8083-8090.*
Wang 1999 "Determination of catecholamines as their N-hydroxysuccinimidyl-3-indolylacetate derivatives by pre-column derivatization HPLC separation and fluorescent detection" FJ Anal Chem 365:682-684.*
Wang 2000 "N-hydrocysuccinimidyl Fluorescein-o-acetate as a fluorescent derivatizing reagent for catecholamines in liquid chromatography" Anal Biochem 281:15-20.*
Liu L, et al. "Simultaneous determination of catecholamines and their metabolites related to Alzheimer's disease in human urine", Journal of Separation Science, vol. 34, No. 10, 2011, pp. 1198-1204.
Mashige F, et al. "[Simultaneous determination of catecholamines, serotonin, and their precursors and metabolites in body fluid by an HPLC system with multi-electrode electrochemical detector].", Rinsho Byori, The Japanese Journal of Clinical Pathology, 1994, vol. 42, No. 6, pp. 591-599.
Herregodts P, et al. "Monoaminergic neurotransmitters in Alzheimer's disease", Journal of Neurological Sciences, vol. 92, No. 1, 1989, pp. 101-116.
International Search Report, dated Oct. 17, 2012, which issued during the prosecution of International Patent Application No. PCT/EP2012/068268, which corresponds to the present application.

* cited by examiner

US 9,606,113 B2

METHOD FOR DIAGNOSING ALZHEIMER'S DISEASE

CROSS-REFERENCE TO RELATED APPLICATIONS

This application is the U.S. national phase of International Application No. PCT/EP2012/068268 filed Sep. 17, 2012 which in turn claims priority to European Patent Application 11306171.7 filed Sep. 16, 2011. The international application published in English as WO 2013/038014 on Mar. 21, 2013. The above applications are herein incorporated by reference.

FIELD OF THE INVENTION

The present invention concerns methods for diagnosing neurodegenerative diseases, in particular Alzheimer's disease.

BACKGROUND

Alzheimer's disease (AD) represents the most common cause of dementia accounting for more than 50% of the cases. It is one of the three diseases which are the most expensive for society, together with cancer and cardiovascular diseases. Alzheimer's disease affects 35 million people worldwide (Querfurth et al. (2010) *New England J. Med.* 362:329-344). Its incidence doubles every 5 years after 65 years of age. Being closely associated with population ageing, AD is an important challenge for research teams.

Currently available medications can produce moderate symptomatic benefits, but at present no treatment is available that can cure AD or at least stop disease progression. Provided that, in the future, novel therapeutics with disease modifying properties become available, most benefit can be expected when the treatment will be started as early as possible in the course of the disease. Obviously, an essential prerequisite will be the availability of improved diagnostic tools allowing for reliable and early, optionally differential diagnosis. It appears that the pathological changes in the AD brain start many years before the first clinical symptoms become obvious (see e.g. Fagan et al. (2009) *Ann. Neurol.* 65:176-83).

Well documented AD biomarkers in cerebrospinal fluid that can support the clinical diagnosis are increased concentrations of total Tau and phosphorylated Tau protein as well as a selective decrease in Aβ1-42 peptide. Furthermore, brain imaging methods, such as Magnetic Resonance Tomography (MRT), Positron Emission Tomography (PET) and in vivo amyloid imaging can provide important additional information. Nevertheless, additional biomarkers or biomarker signatures and novel analytical methods are required to improve the early and/or differential diagnosis to reliably detect AD patients at early disease stages or at high risk.

Diagnostic tests are defined in terms of their sensitivity (defined by the percentage of patients suffering from the disease and tested as positive, in a population of patients identified as suffering from said disease using a reference test) and by their specificity (defined by the percentage of patients who do not suffer from the disease and who were tested as negative, in a population of patients identified as not suffering from said disease using a reference test). Diagnostic tests with a high sensitivity and a high specificity (close to 100%) are rare.

Accordingly, there is still a need for methods enabling a specific and sensitive diagnosis of Alzheimer's disease, in particular an early diagnosis of the disease, before the onset of clinical symptoms.

SUMMARY

The present inventors have demonstrated that such a diagnostic method could be obtained by measuring and combining the levels of at least two catecholamines in a sample obtained from a biological fluid of a subject to be diagnosed. Another advantage is certainly that the present method might finally be cheap and available.

Without willing to be bound by theory, it is further of the inventors' opinion that the measurement of catecholamines could even be an early indicator of a neurodegenerative disease because catecholamines producing cells (locus coerulus) are possibly affected very early in the disease process.

Catecholamines are hormones released by the adrenal glands, which are part of the sympathetic nervous system and contain a catechol or 3,4-dihydroxyphenyl group.

Some previous studies aimed to determine whether a link existed between catecholamines and Alzheimer's disease. However, no clear correlation between these compounds and Alzheimer's disease has been demonstrated so far. Indeed, even if techniques to assay catecholamine levels in different biological samples are now within the general knowledge of the skilled person, numerous contradictory results have been obtained. For example, Peskind et al. (1998) *Neuropsychopharmacology* 19:465-471 demonstrated that the concentration of epinephrine in cerebrospinal fluid was higher in patients suffering from Alzheimer's disease than in older or young subjects while Adolfsson et al. (1979) *Brit. J. Psychiatry* 135:216-223 demonstrated that the mean correlation of norepinephrine was lower in the brain of patients suffering from Alzheimer's disease. Accordingly, in view of these results, catecholamines were not considered as potential markers of Alzheimer's disease.

Additionally, to the inventors' knowledge, no previous study proposed associating or combining the levels of catecholamines to diagnose Alzheimer's disease in a subject.

Specifically, the present invention is based on quantifying catecholamines by a single method involving the combination of the respective levels of at least two catecholamines, performed directly on samples from a biological fluid of a patient.

The present invention thus relates to a method, in particular an in vitro method, for diagnosing a neurodegenerative disease, preferably Alzheimer's disease, in a subject, including the steps of:
a1) measuring the level of each of at least two catecholamines in a sample of biological fluid from said subject;
a2) determining a virtual value by combining the levels measured in step a1) preferably applying one of the following algorithms:

$$V = \frac{[i]}{([i]+[ii]+[iii])}; V = \frac{[i]}{([ii]+[iii])}; V = \frac{[ii]}{([i]+[ii]+[iii])}; V = \frac{[ii]}{([i]+[iii])};$$

-continued $$V = \frac{[iii]}{([i]+[ii]+[iii])}; V = \frac{[iii]}{([i]+[ii])}; V = \frac{([i]+[ii])}{([i]+[ii]+[iii])}; V = \frac{([i]+[ii])}{([i]+[iii])}; V = \frac{([i]+[ii])}{([i]+[iii])};$$

$$V = \frac{([i]+[ii])}{[iii]}; V = \frac{([i]+[iii])}{([i]+[ii]+[iii])}; V = \frac{([i]+[iii])}{([ii]+[iii])}; V = \frac{([i]+[iii])}{([ii]+[i])}; V = \frac{([i]+[iii])}{[ii]};$$

$$V = \frac{([ii]+[iii])}{([i]+[ii]+[iii])}; V = \frac{([ii]+[iii])}{([i]+[iii])}; V = \frac{([ii]+[iii])}{([i]+[ii])}; V = \frac{([ii]+[iii])}{[i]}; \text{ or } V = [i] + [ii] + [iii];$$

wherein V is the virtual value to be determined and [x] is the respective level of one of said catecholamines, x being i, ii or iii, and b) based on the virtual value determined in step a2), determining whether said subject suffers from a neurodegenerative disease, preferably Alzheimer's disease;

or a1) measuring the global level of at least two catecholamines in a sample of biological fluid from said subject; and b') based on the global level measured in step a'1), determining whether said subject suffers from a neurodegenerative disease, preferably Alzheimer's disease.

The invention will be further illustrated by the following figures and examples.

$$R = \frac{K \times [A\beta 1 - 42]}{\sum Ac(Cath)} - 1,$$

wherein K is a constant equal to 7,000, [Aβ1-42] represents the concentration of Aβ1-42 and ΣAc(Cath) represents the sum of the corrected areas corresponding to adrenaline, noradrenaline and dopamine. The dashed line represents the separation between patients suffering from Alzheimer's disease and non-demented patients.

Figure 5:
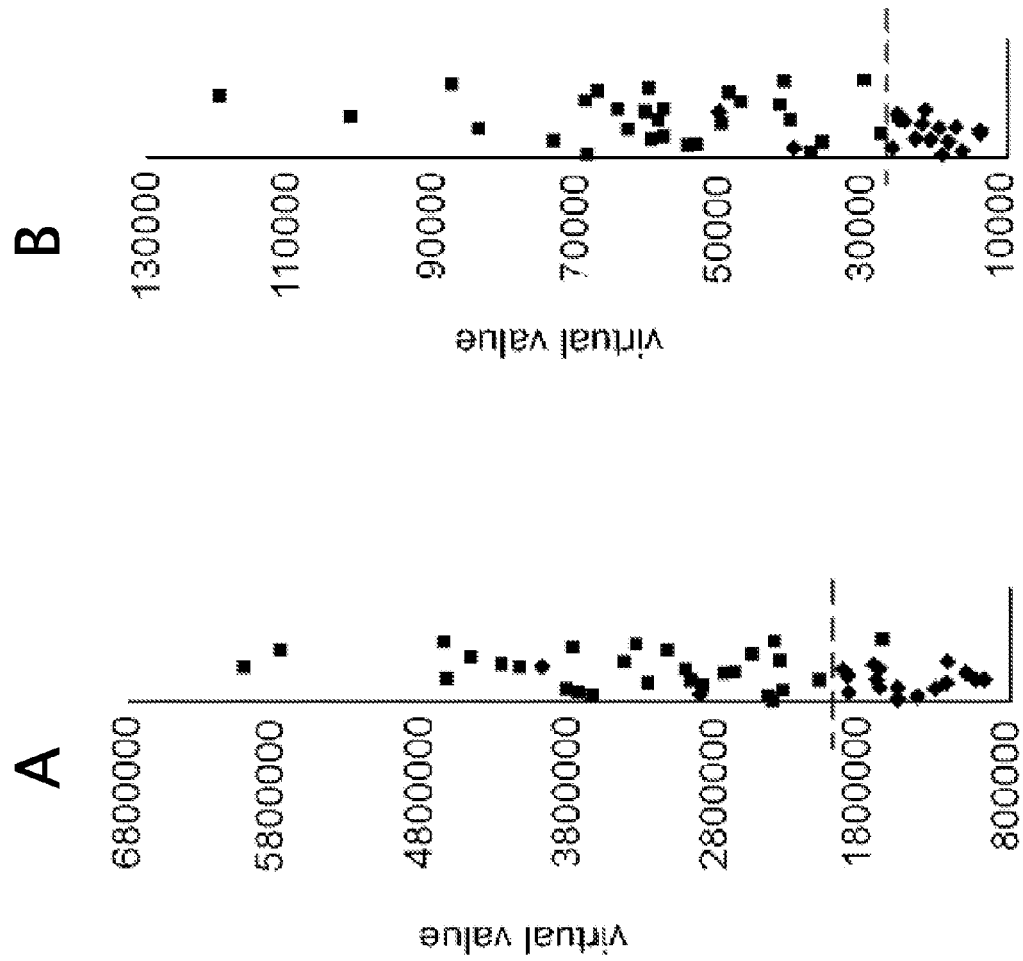

FIG. 5 shows a diagram representing in abscissa the distribution of the CSF samples analyzed in Example 3 obtained from non-demented patients, which are patients considered as not suffering from Alzheimer's disease by a conventional diagnostic test (squares) and patients considered as suffering from Alzheimer's disease by a conventional diagnostic test (rhombs), and the virtual value obtained applying the following algorithms in ordinate:

(A) V=ΣAc(Cath), where ΣAc(Cath) represents the sum of the corrected areas corresponding to adrenaline, noradrenaline and dopamine;

$$(B)\ V = \frac{\sum Ac(Cath)}{age},$$

where ΣAc(Cath) represents the sum of the corrected areas corresponding to adrenaline, noradrenaline and dopamine.

The dashed lines represent the separation between patients suffering from Alzheimer's disease and non-demented patients.

Figure 6:
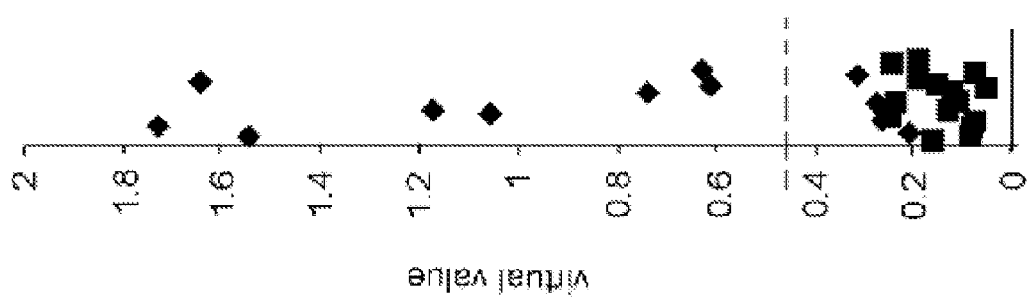

FIG. 6 shows a diagram representing in abscissa the distribution of the CSF samples analyzed in Example 5 obtained from non-demented patients, which are patients considered as not suffering from Alzheimer's disease by a conventional diagnostic test (squares) and patients considered as suffering from Alzheimer's disease by a conventional diagnostic test (rhombs), and the virtual value obtained applying the following algorithm in ordinate:

$$score1 = \sum Ac(Cath)$$

$$score2 = \frac{\sum Ac(Cath)}{age}$$

$$score3 = \frac{K1 \times [A\beta 1 - 42]}{\sum Ac(Cath)}$$

$$score4 = \frac{K2 \times [Tau]}{\sum Ac(Cath)}$$

wherein K1 is a constant equal to 7,000, [Aβ1-42] represents the concentration of Aβ1-42, K2 is a constant equal to 15,000, [Tau] represents the concentration of Tau, and ΣAc(Cath) represents the sum of the corrected areas corresponding to adrenaline, noradrenaline and dopamine.

The dashed line represents the separation between patients suffering from Alzheimer's disease and non-demented patients.

Score 1, score 2, score 3 and score 4 were calculated using iterative algorithm or in the same time in a genetic algorithm context; in order to exclude positive or negative false to increase the discrimination power of the test.

Figure 7:
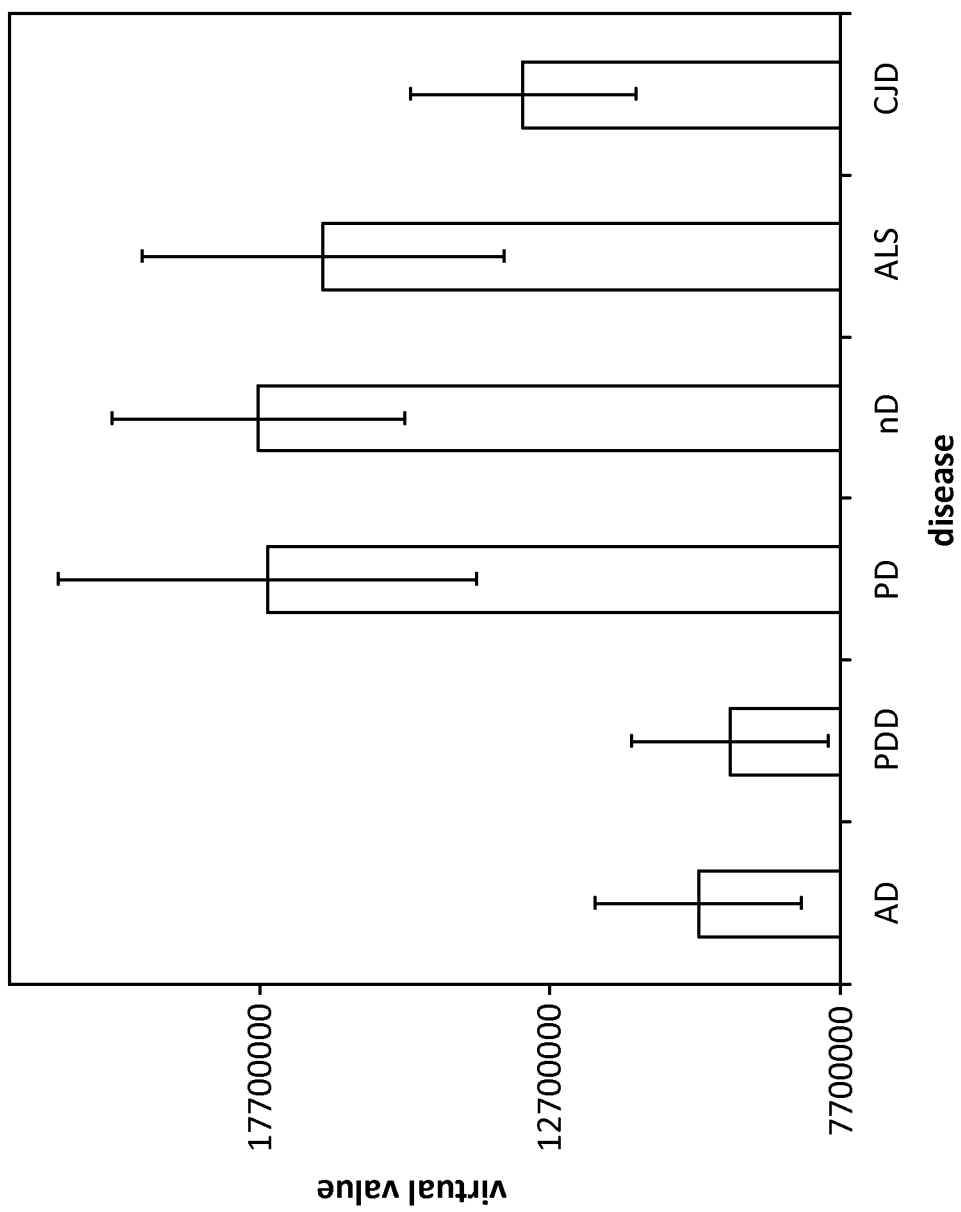

FIG. 7 shows histograms representing the virtual value obtained by summing the corrected areas of the catecholamines in the 47 subjects of Example 6, according to the disease of the patient (AD: Alzheimer's disease, PDD: Parkinson disease with dementia, PD: Parkinson disease, nD: control patients suffering from pathologies without associated dementias, ALS: amyloid lateral sclerosis and CJD: Creutzvelt-Jacob disease).

Figure 8:
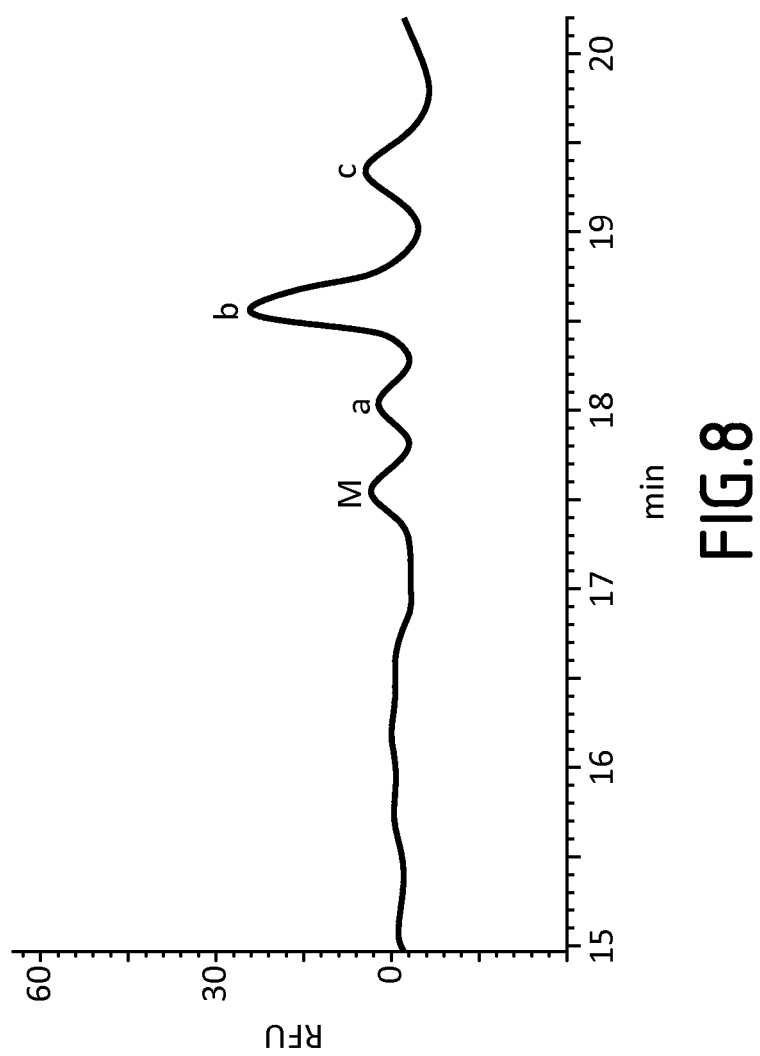

FIG. 8 shows the electrophoretic profile obtained from the analysis of a cerebrospinal fluid (CSF) sample derivatized by FluoProbe® as described in Example 1. The letters show the peaks corresponding to ubiquitin and catecholamines. a represents adrenaline; b noradrenaline, c dopamine and M: ubiquitin.

Figure 9:
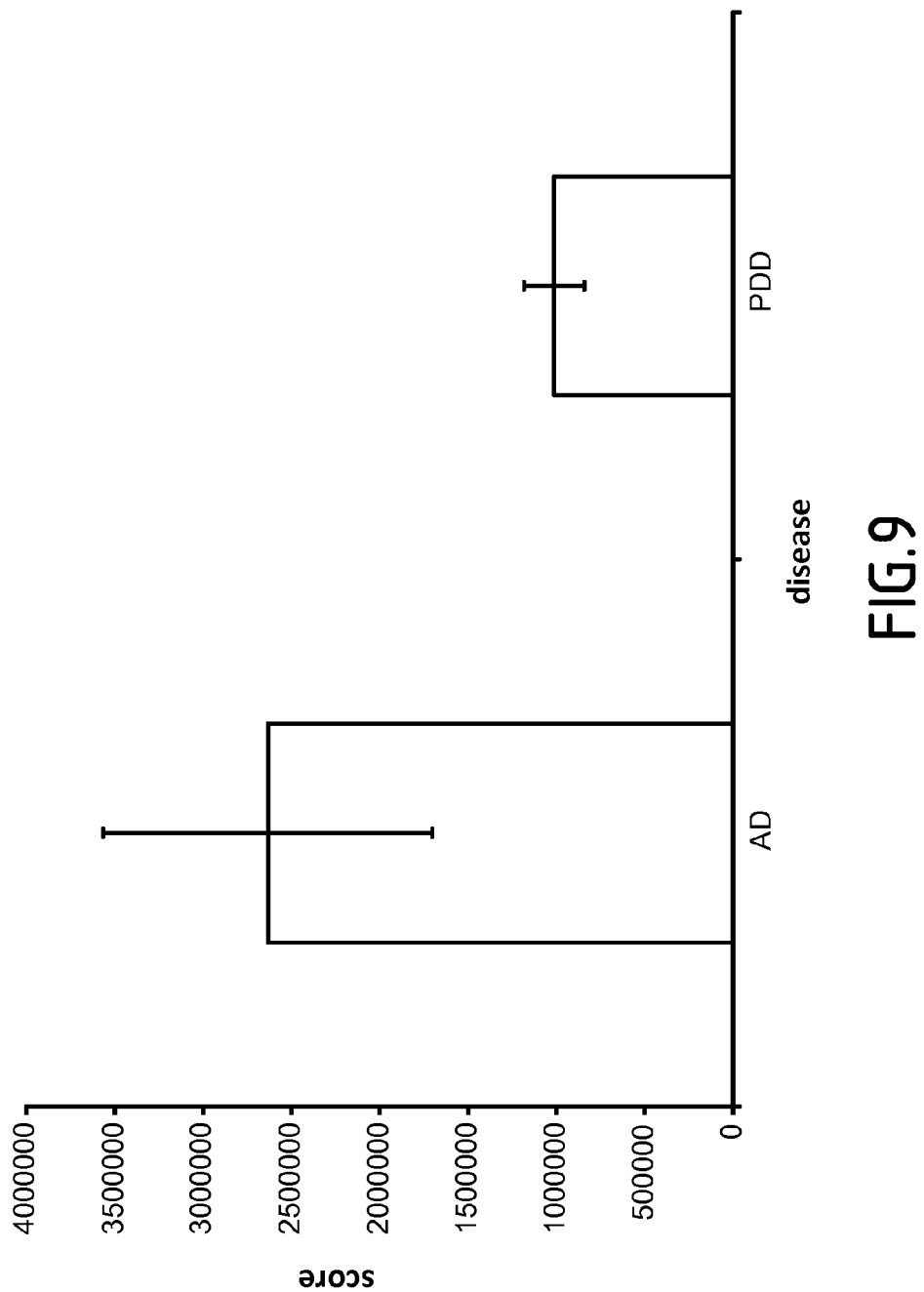

FIG. 9 shows histograms representing the level of ubiquitin (score) obtained in the subjects of Example 6 suffering from Alzheimer's disease (AD) or Parkinson disease with dementia (PDD).

DETAILED DESCRIPTION

Diagnosis of a Neurodegenerative Disease

As intended herein, the term "diagnosis" relates to a method for determining the pathology afflicting a subject.

In the context of the present invention, a "subject" denotes a human or non-human mammal, such as a rodent (rat, mouse, rabbit), a primate (chimpanzee), a feline (cat), a canine (dog). Preferably, the subject is human.

In a preferred embodiment, the subject presents signs of dementia.

As used herein, the term "dementia" refers to a serious loss of global cognitive ability in a previously unimpaired person, beyond what might be expected from normal aging. Preferably, said subject has been previously diagnosed as presented signs of dementia, in particular by cognitive testing.

As known from the skilled person, dementia is not a single disease, but rather a non-specific illness syndrome (i.e., set of signs and symptoms) in which affected areas of cognition may be memory, attention, language, and problem solving.

The method of the invention has the advantage of enabling diagnosing specifically Alzheimer's disease in a patient already presenting signs of dementia, thereby enabling discriminating Alzheimer's disease from other forms of dementia such as Parkinson disease, Parkinson disease with dementia, amyotrophic lateral sclerosis, Creutzfeldt-Jacob's disease, mental depression, vascular dementia, frontotemporal dementia, semantic dementia and dementia with Lewy bodies.

As used herein, the expression "sample of biological fluid" encompasses all samples of body fluids which can be obtained from a subject. The sample of biological fluid may in particular be selected from the group consisting of cerebrospinal fluid (CSF) sample, blood sample, serum, plasma, urine and saliva sample. Preferably, the sample of biological fluid is CSF sample.

As used herein, the expression "neurodegenerative disease" refers to a disease or condition characterized by neuronal degeneration and clinically by problems with movements, affecting cognitive abilities such as memory, or related to all types of dementia. In particular, a neurodegenerative disease may be associated with impairment, loss or potential loss of cognitive abilities and/or impairment or loss of brain cells. Neurodegenerative diseases are well-known from the skilled person and include Alzheimer's disease, frontotemporal dementia, dementia with Lewy bodies, corticobasal degeneration, progressive supranuclear palsy, prion disorders such as Creutzfeldt-Jakob disease, Parkinson's disease, Huntington's disease, multiple system atrophy, amyotrophic lateral sclerosis, hereditary spastic paraparesis, spinocerebellar atrophies, Friedreich's ataxia, multiple sclerosis, Charcot Marie Tooth, ALS/PCD of Guam, Down syndrome, myotonic dystrophy, Pick's disease, postencephalitic parkinsonism, primary progressive ataxia, subacute sclerosis panencephalitis, FTD-17, argyrophilic grain disease, type C Niemann-Pick's disease, Hallervorden-Spatz disease, subacute sclerosing panencephalitis, Fukuyama congenital muscular dystrophy, Kufs's disease, Cockayne syndrome, Williams syndrome, mental depression and inclusion body myositis. More particularly, the neurodegenerative disease according to the invention may be selected from the group consisting of Alzheimer's disease, Parkinson's disease, Creutzfeldt-Jakob disease, frontotemporal dementia, dementia with Lewy bodies, amyotrophic lateral sclerosis (ALS), mental depression, Huntington's disease and mild cognitive impairment (MCI).

Preferably, the neurodegenerative disease is selected from the group consisting of Alzheimer's disease, Parkinson's disease, Creutzfeldt-Jakob disease, frontotemporal dementia, dementia with Lewy bodies. More preferably, the neurodegenerative disease is Alzheimer's disease.

As used herein, the term "Alzheimer's disease" refers to a neurodegenerative disease associated with the accumulation of β-amyloid peptides in the brain, specifically, in the gray matter of the brain, forming β-amyloid peptide deposits or plaques, and with neurofibrillary tangles composed of hyperphosphorylated Tau protein.

Alzheimer's disease (AD) may be divided into three phases of Alzheimer's disease progression over time: pre-clinical Alzheimer's disease, mild cognitive impairment (MCI) or pre-dementia due to Alzheimer's disease and dementia due to Alzheimer's disease (McKhann et al. (1984) Neurology, 34, 939-44).

Preclinical Alzheimer's disease, which is the first phase of AD, is characterized by a state where clinical symptoms or cognitive difficulties are no detectable according to the currently used methods. This stage, which can appear until 20 or 30 years before the first pre-clinical symptoms, already involves biochemical metabolism disorders inducing biological compounds change in term of their respective level or their conformational states in different biological fluids (Jack Jr et al. (2010) *Lancet. Neurol.* 9:119-147).

Pre-dementia is characterized by mild cognitive difficulties that may appear up to eight years before a person fulfills the conventional clinical criteria for diagnosis of AD. The most noticeable deficit is memory loss, which shows up as difficulty in remembering recently learned facts and inability to acquire new information. Subtle problems with the executive functions of attentiveness, planning, flexibility, and abstract thinking, or impairments in semantic memory (memory of meanings and concept relationships) can also be symptomatic of the early stages of AD. This pre-dementia step may also be named mild cognitive impairment (MCI).

Dementia due to Alzheimer's Disease includes the three following stages:

Early Alzheimer's disease corresponds to the stage in which impairment of learning and memory has increased enough to establish a conventional definitive diagnosis. In this stage, the patient is usually capable of adequately communicating basic ideas. While performing fine motor tasks such as writing, drawing or dressing, certain movement coordination and planning difficulties may be present but they are commonly unnoticed.

Moderate Alzheimer's disease corresponds to the stage in which progressive deterioration makes the patients unable to perform most common activities of daily living. Speech difficulties become evident due to an inability to recall vocabulary, which leads to frequent incorrect word substitutions. Reading and writing skills are also progressively lost. Complex motor sequences become less coordinated. During this phase, memory problems worsen, and the person may fail to recognize close relatives (Förstl and Kurz (1999) *European Archives of Psychiatry and Clinical Neuroscience* 249: 288-290). Long-term memory, which was previously intact, becomes impaired. Behavioral and neuropsychiatric changes become more prevalent. Common manifestations are wandering, irritability and labile affect, leading to crying, outbursts of unpremeditated aggression or resistance to care-giving.

Advanced Alzheimer's disease corresponds to the last stage of the disease in which the patient is completely dependent upon caregivers. Language is reduced to simple phrases or even single words, eventually leading to complete loss of speech. Although aggressiveness can still be present, extreme apathy and exhaustion are much more common results.

Advantageously, the method of diagnosis according to the invention could enable establishing a diagnosis of Alzheimer's disease before the onset of the symptoms, as soon as during the pre-dementia or early Alzheimer's disease.

Catecholamines

In the context of the invention, the term "catecholamine" refers to hormones released by the adrenal glands, which are part of the sympathetic nervous system and contain a catechol or 3,4-dihydroxyphenyl group. They have more specifically the distinct structure of a benzene ring with two hydroxyl groups, an intermediate ethyl chain and a terminal amine group. Catecholamines include in particular adrenaline (also called epinephrine), noradrenaline (also called norepinephrine), and dopamine, all of which are produced from phenylalanine and tyrosine.

As used herein, the term "dopamine" refers to a catecholamine neurotransmitter or hormone which is typically of the following formula (I):

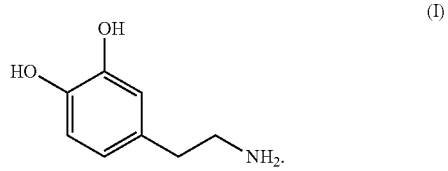 [SMILES: NCCc1ccc(O)c(O)c1]
(I)

As used herein, the terms "adrenaline" and "epinephrine" are used indifferently and refer to a hormone and neurotransmitter which is synthesized by methylation of noradrenaline. Adrenaline is typically of the following formula (II):

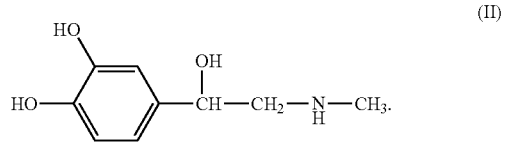
(II)

As used herein, the terms "noradrenaline" and "norepinephrine" are used indifferently and refer to a neurotransmitter which is synthesized from dopamine by dopamine β-hydroxylase. Noradrenaline is typically of the following formula (III):

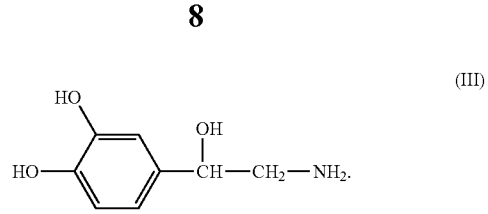
(III)

In the context of the invention, the term "catecholamine" encompasses both the native compounds, as defined herein above, and the corresponding derivatized compounds.

As used herein, the term "derivatized" or "derivatization" refers to the transformation of a chemical compound into a product (the derivatized compound) of similar chemical structure but bearing deviation in terms of structures and properties of the initial compound such as global charges of molecules, reactivity, solubility, optical properties, boiling point, melting point, aggregate state, or chemical composition. Resulting new chemical properties can be used for quantification or separation of the derivatized product. Preferably, the catecholamines of the invention are derivatized with a fluorophore enabling their detection, such as a fluorophore comprising a reactive NHS moiety, preferably Fluoprobe®, Alexa Fluor® 488 or FAM X-SE, or a fluorophore comprising a reactive isothiocyanate-type moiety, preferably FITC or 5-FITC.

In a preferred embodiment of the present invention, the level of each of at least two catecholamines selected from the group consisting of dopamine, adrenaline and noradrenaline is measured in step a1). In another preferred embodiment, the global level of at least two catecholamines selected from the group consisting of dopamine, adrenaline and noradrenaline is measured in step a'1). In a still preferred embodiment of the present invention, the level of each of at least dopamine, adrenaline and noradrenaline is measured in step a1). In a still preferred embodiment, the global level of at least dopamine, adrenaline and noradrenaline is measured in step a'1).

Step of Measuring the Level of at Least Two Catecholamines

As used herein, the term "level" of a biochemical marker refers to the concentration, the amount or the activity of the biochemical marker. It may also refer to the signal intensity produced by said biochemical marker when measured by a measurement device. Indeed, as known from the skilled person, the concentration, the amount or the activity of a given biochemical marker may be easily obtained from the signal intensity produced by said biochemical marker when measured by a measurement device, for example by comparing said signal intensity with a standard curve or with a calibrator. In particular, when the level of the biochemical marker is measured by capillary electrophoresis, this level may correspond to the corrected area measured for this biochemical marker, i.e. to the ratio between the area measured for this biochemical marker and the migration time corresponding to this biochemical marker. Indeed, as well known from the skilled person, the concentration of a compound may be obtained from its absorbance, its luminescence such as fluorescence emission, its intrinsic chemical properties such as conductivity or redox potentiality, through logarithmic or linear dependences between the two variables.

Preferably, in the context of the invention, the level of a biochemical marker refers to the amount or concentration of the biochemical marker, more particularly to the molar or the mass amount or to the molar or the mass concentration of the biochemical marker.

As used herein, the expression "measuring the level of each of at least two catecholamines" means that the level of each marker is measured separately. As known from the skilled person, since catecholamines represent a family of compounds sharing a similar chemical backbone, it is possible to determine the global level of catecholamines present in a biological sample without differentiating the specific levels of each catecholamine. Nevertheless, in a particular embodiment of the present invention, the level of each of the at least two catecholamines is determined individually, even though the levels of each of the at least two catecholamines can be measured in a single experiment using a single measurement device under simultaneous analysis conditions.

As used herein, the expression "measuring the global level of at least two catecholamines" means that the global level of at least two catecholamines present in a biological sample is measured without differentiating the specific levels of each catecholamine. Such a global measurement enables decreasing the time of analysis of the biological sample, in particular when the levels are measured by electrophoresis.

Techniques to measure the level of a compound in a biological sample, in particular in a sample from a biological fluid, are well-known from the skilled person. Examples of suitable techniques include electrophoresis, in particular gel electrophoresis or capillary electrophoresis, spectrometry such as mass spectrometry or spectrofluorimetry, chromatography such as high performance liquid chromatography (HPLC) or ultra high performance liquid chromatography (UHPLC) and their combinations (LC/MS, GC/MS), immunoassay techniques and electrochemistry-based techniques.

Preferably, the step of measuring the level of each of the at least two catecholamines in step a1) or the step of measuring the global level of at least two catecholamines in step a'1) is performed by capillary electrophoresis.

As used herein, the expression "capillary electrophoresis" refers to a group of high performance separation techniques that employ narrow-bore fused-silica capillaries (coated or uncoated) for the separation of species through the application of an electric field. Capillary electrophoresis includes in particular capillary zone electrophoresis (CZE), capillary gel electrophoresis (CGE), capillary electrochromatography (CEC), capillary isoelectric focusing (CIEF), capillary isotachophoresis (CITP) and micellar electrokinetic capillary chromatography (MEKC).

In Capillary zone Electrophoresis (CZE), two processes take place: (i) the mechanism by which the species are separated is called electromigration and is dependent on their charge to hydrodynamic volume, and (ii) the mechanism by which the background electrolyte migrates through the capillary is called electroosmosis. The cause by which the species are separated depends on both their electrophoretic mobility (m/z) and electroosmotic flow (EOF). These parameters are vectors, and modules can be added or subtracted depending on their direction. Classical CZE requires that the analyte is charged.

In Capillary Gel Electrophoresis (CGE), neutrally coated fused silica capillaries are repeatedly refilled with a linear polymer-gel/buffer system. In addition to the classical CZE separation mechanism, there is a sieving effect from the polymer gel matrix and also sometimes complexation effects with surfactants.

In Micellar Electrokinetic Capillary Chromatography (MEKC), micelles are employed in the background electrolyte (BGE) and analytes partition themselves between micelles and the bulk electrolyte.

Capillary Electrochromatography (CEC) utilizes capillary channels filled with a stationary phase (porous media like, spherical packing materials or monolithic structures), combining retention mechanisms on the stationary phase and electromigration.

In Capillary Isoelectric Focusing (CIEF), the analytes separate according to their isoelectric point in a capillary in which a pH gradient is established.

In a preferred embodiment, the step of measuring the level of each of the at least two catecholamines in step a1) or the step of measuring the global level of the at least two catecholamines in step a'1) is performed by capillary electrophoresis coupled to fluorescence detection.

As used herein, the expression "fluorescence detection" refers to optical detection techniques wherein the compound to be examined is detected via the fluorescence it emits after excitation with an excitation source. Examples of fluorescence detection are well-known from the skilled person and include laser-induced fluorescence detection, lamp-based fluorescence detection, light emitting diode induced fluorescence detection.

In a preferred embodiment, the step of measuring the level of each of the at least two catecholamines in step a1) or the step of measuring the global level of the at least two catecholamines in step a'1) is performed by capillary electrophoresis coupled to laser-induced fluorescence, more preferably by capillary zone electrophoresis coupled to laser-induced fluorescence.

As used herein, the term "laser-induced fluorescence" or LIF refers to a spectroscopic method used for studying structure of molecules, detection of selective species, flow visualization and measurements. The species to be examined is excited with a laser. The excited species will after some time, usually in the order of few nanoseconds to microseconds, de-excite and emit light at a wavelength larger than the excitation wavelength. This light, fluorescence, is then measured.

In a preferred embodiment, the step a1) of measuring the level of each of the at least two catecholamines is implemented at least twice, more preferably at least three times. Preferably, the step a2) of determining a virtual value is then carried out after each implementation of step a1). The virtual value used in step b) is then preferably the mean of the virtual values determined in each step a2).

The inventors demonstrated that such an embodiment enabled decreasing the coefficient of variation associated with the measurement of catecholamines levels, independently of the technique of measure used. Such a decrease therefore enables obtaining a method of diagnosis with a high power of diagnosis.

Measurement of Other Known Markers of Neurodegenerative Disease

The inventors demonstrated that measuring the level of each of at least two catecholamines or measuring the global level of at least two catecholamines in addition to known markers of neurodegenerative disease, preferably Alzheimer's disease, and/or compounds known to be associated with neurodegenerative disease, preferably Alzheimer's disease, and/or the value of parameters known to be associated with neurodegenerative disease, preferably Alzheimer's disease, enabled highly improving the specificity and sensitivity of previous methods of diagnosis which only used said known markers of neurodegenerative disease, preferably Alzheimer's disease.

Accordingly, in a particular embodiment, the level of at least one other known marker of said neurodegenerative disease, preferably Alzheimer's disease, and/or at least one other compound known to be associated with said neurodegenerative disease, preferably Alzheimer's disease, is further measured in the sample of biological fluid from said subject, and/or the value of at least one other parameter known to be associated with said neurodegenerative disease, preferably Alzheimer's disease, is further determined in said subject, in step a1) or in step a'1).

As used herein, the expression "known marker of neurodegenerative disease" refers to compounds which have previously been used in methods for diagnosing or assisting diagnosis of neurodegenerative diseases. Such markers are well-known from the skilled person and are described in literature. Known markers of neurodegenerative disease according to the invention include in particular β-amyloid peptides Aβ1-42 and tau protein including unphosphorylated tau protein and phosphorylated tau protein, in particular phosphorylated tau 181.

As used herein, the expression "compound known to be associated with neurodegenerative disease" refers to compounds which have previously been demonstrated to be linked with a neurodegenerative disease, in particular compounds which have previously been shown to be differentially present in patients suffering from a neurodegenerative disease compared to patients not suffering from said neurodegenerative disease. Such compounds are well-known from the skilled person and are described in literature. Compounds known to be associated with neurodegenerative disease according to the invention include in particular N-terminal truncated forms of β-amyloid peptide and fragments thereof, Aβ autoantibodies, sAPPβ, sAPPα, cholesterol, oxysterols, 24S gydroxycholesterol, apoplipoprotein E, antioxidants such as vitamins C, E and A, lycopene, β-carotene, urate, bilirubin, isoprostanes, 8,12-iso-iPF2α-VI, α1-antichymotrypsin, interleukin-3, interleukin-6, soluble interleukin-6 receptor complex, C-terminal endothelin-1 precursor fragment, midregional pro-adrenomedullin, midregional pro-atrial natriuretic peptide, small molecules such as monoamines, hormones and neurotransmitters such as glutamate, GABA, histamine, agmatine, β-phenylethylamine (PEA); serotonin and oxytocin, ubiquitin, FK506-binding protein 52 (FKBP52), fatty acid binding 3 protein (H-FABP), S100 calcium binding protein B (S-100B), RNA-binding protein FUS (FUS), Erk1, Erk2, Glial Fibrillary Acidic Protein (GFAP), clusterin, formaldehyde, thymosin and protein kinase R (PKR). Preferably, compounds known to be associated with neurodegenerative disease according to the invention are selected from the group consisting of ubiquitin, sAPPβ, FKBP52, HPAPB, S-100B, FUS, Erk1, Erk2, GFAP, formaldehyde, thymosin and PKR. Still preferably, known markers of a neurodegenerative disease and/or compounds known to be associated with a neurodegenerative disease according to the invention are selected from the group consisting of ubiquitin, Aβ1-42, phosphorylated tau 181, unphosphotylated tau protein, sAPPβ, FKBP52, HPAPB, 5-100B, FUS, Erk1, Erk2, GFAP, formaldehyde, thymosin and PKR.

More particularly, known markers of Alzheimer's disease and/or compounds known to be associated with Alzheimer's disease according to the invention are preferably selected from the group consisting of ubiquitin, Aβ1-42, sAPPβ, phosphorylated tau 181, unphosphorylated tau protein and FKBP52. Known markers of Parkinson's disease and/or compounds known to be associated with Parkinson's disease according to the invention are preferably selected from the group consisting of phosphorylated tau 181 and unphosphorylated tau protein. Known markers of Creutzfeldt-Jakob disease and/or compounds known to be associated with Creutzfeldt-Jakob disease according to the invention are preferably selected from the group consisting of ubiquitin. Known markers of frontotemporal dementia and/or compounds known to be associated with frontotemporal dementia according to the invention are preferably selected from the group consisting of phosphorylated tau 181 and unphosphorylated tau protein.

As used herein, the expression "parameter known to be associated with a neurodegenerative disease, preferably Alzheimer's disease" refers to parameters from a subject which have previously been demonstrated to be linked with a neurodegenerative disease, preferably Alzheimer's disease. Such parameters may be quantitative or qualitative. Such parameters are well-known from the skilled person and are described in literature. Parameters known to be associated with a neurodegenerative disease, preferably Alzheimer's disease, according to the invention include in particular result of a cognitive test, age and sex.

As used herein, the term "cognitive test" refers to assessments of the cognitive capabilities of humans and animals. Cognitive tests used in the context of the invention can be for example the mini-mental state examination (MMSE).

Preferably, in the methods of the invention, the levels or values of at least two, more preferably at least three, still preferably at least four, other known markers of Alzheimer's disease and/or compounds known to be associated with Alzheimer's disease and/or parameters known to be associated with Alzheimer's disease, being preferably selected from the group consisting of ubiquitin, Aβ1-42, sAPPβ, phosphorylated tau 181, unphosphorylated tau protein, FKBP52, age, sex and cognitive tests, are further determined at step a1) or a'1).

Preferably, in the methods of the invention the age of the patient is determined in step a1) or a'1).

Still preferably, in the methods of the invention, the levels of Aβ1-42 and/or phosphorylated tau 181 are measured at step a1) or a'1).

Most preferably, in the methods of the invention, the levels of Aβ11-42 and/or phosphorylated tau 181 and/or the age of the patient are determined in step a1) or a'1).

Step of Determining a Virtual Value

As used herein, the expression "combining levels" or "combination of levels" refers to applying an algorithm to the levels measured in step a1) in order to obtain a virtual value which enables establishing the diagnosis of a neurodegenerative disease, preferably Alzheimer's disease, as defined above. More particularly, combining the levels measured in step a1) may correspond to:
  (i) summing the levels measured in step a1),
  (ii) determining a ratio of the levels measured in step a1), such as:
    a ratio of the level of one catecholamine on the level of another catecholamine, in particular a ratio of the level of dopamine on the level of adrenaline, a ratio of the level of dopamine on the level of noradrenaline, a ratio of the level of adrenaline on the level of noradrenaline, a ratio of the level of adrenaline on the level of dopamine, a ratio of the level of noradrenaline on the level of dopamine, or a ratio of the level of noradrenaline on the level of adrenaline;
a ratio of the level of one catecholamine on the sum of the levels of two other catecholamines, in particular a ratio of the level of dopamine on the sum of the levels of adrenaline and noradrenaline, a ratio of the level of adrenaline on the sum of the levels of dopamine and noradrenaline or a ratio of the level of noradrenaline on the sum of the levels of dopamine and noradrenaline;
a ratio of the sum of the levels of two catecholamines on the level of another catecholamine, in particular a ratio of the sum of the levels of dopamine and adrenaline on the level of noradrenaline, a ratio of the sum of the levels of dopamine and noradrenaline on the level of adrenaline, or a ratio of the sum of the levels of adrenaline and noradrenaline on the level of dopamine;
a ratio of the level of one catecholamine on the sum of the levels of three catecholamines, in particular a ratio of the level of dopamine on the sum of the levels of dopamine, adrenaline and noradrenaline, a ratio of the level of adrenaline on the sum of the levels of dopamine, adrenaline and noradrenaline or a ratio of the level of noradrenaline on the sum of the levels of dopamine, adrenaline and noradrenaline;
a ratio of the sum of the levels of three catecholamines on the level of one catecholamine, in particular a ratio of the sum of the levels of dopamine, adrenaline and noradrenaline on the level of dopamine, a ratio of the sum of the levels of dopamine, adrenaline and noradrenaline on the level of adrenaline, or a ratio of the sum of the levels of dopamine, adrenaline and noradrenaline on the level of noradrenaline;
a ratio of the sum of the levels of two catecholamines on the sum of the levels of three catecholamines, in particular a ratio of the sum of the levels of dopamine and adrenaline on the sum of the levels of dopamine, adrenaline and noradrenaline, a ratio of the sum of the levels of dopamine and noradrenaline on the sum of the levels of dopamine, adrenaline and noradrenaline or a ratio of the sum of the levels of adrenaline and noradrenaline on the sum of the levels of dopamine, adrenaline and noradrenaline;
a ratio of the sum of the levels of three catecholamines on the sum of the levels of two catecholamines, in particular a ratio of the sum of the levels of dopamine, adrenaline and noradrenaline on the sum of the levels of dopamine and adrenaline, a ratio of the sum of the levels of dopamine, adrenaline and noradrenaline on the sum of the levels of dopamine and noradrenaline or a ratio of the sum of the levels of dopamine, adrenaline and noradrenaline on the sum of the levels of adrenaline and noradrenaline; or
(iii) applying one of the following algorithms:

$$V = \frac{[i]}{([i]+[ii]+[iii])}; V = \frac{[i]}{([ii]+[iii])}; V = \frac{[ii]}{([i]+[ii]+[iii])};$$

$$V = \frac{[ii]}{([i]+[iii])}; V = \frac{[iii]}{([i]+[ii]+[iii])}; V = \frac{[iii]}{([i]+[ii])};$$

$$V = \frac{([i]+[ii])}{([i]+[ii]+[iii])}; V = \frac{([i]+[ii])}{([ii]+[iii])}; V = \frac{([i]+[ii])}{([i]+[iii])};$$

$$V = \frac{([i]+[ii])}{[iii]}; V = \frac{([i]+[iii])}{([i]+[ii]+[iii])}; V = \frac{([i]+[iii])}{([ii]+[iii])};$$

$$V = \frac{([i]+[iii])}{([ii]+[i])}; V = \frac{([i]+[iii])}{[ii]}; V = \frac{([ii]+[iii])}{([i]+[ii]+[iii])};$$

$$V = \frac{([ii]+[iii])}{([i]+[iii])}; V = \frac{([ii]+[iii])}{([i]+[ii])}; V = \frac{([ii]+[iii])}{[i]}; \text{ or}$$

$$V = [i]+[ii]+[iii];$$

wherein V is the virtual value to be determined and [x] is the respective level of one of the above defined catecholamines, x being i, ii or iii.

The present invention indeed arises from the unexpected finding by the inventors that summing the levels, in particular the concentrations, of at least two catecholamines from a sample of biological fluid from a subject enables establishing a diagnosis of a neurodegenerative disease, preferably Alzheimer's disease, with a much better specificity and sensitivity than when using each catecholamine separately. More specifically, and without willing to be bound by the theory, it seems that catecholamines act in synergy to enable establishing a diagnosis.

Preferably, when the step a1) of the methods of the invention consists in measuring the level of each of dopamine, adrenaline and noradrenaline, combining the levels measured in step a1) means summing the levels of dopamine, adrenaline and noradrenaline measured in step a1).

As used herein, the expression "virtual value" refers to the value obtained by combining the levels measured in step a1) as defined above. As known by the skilled person, the nature of the virtual value and its unity will depend on the algorithm used to combine the levels measured in step a1).

Step of Determination of a Score

In a preferred embodiment, the methods of the invention further comprise a step a2b) of determining a score by combining the virtual value as defined herein above in section "Step of determining a virtual value" above, determined in step a2), or the global level, as defined herein above in section "Step of measuring the level of at least two catecholamines", determined in step a'1), and the level of the at least one other known marker of the neurodegenerative disease, preferably Alzheimer's disease, and/or of the at least one other compound known to be associated with the neurodegenerative disease, preferably Alzheimer's disease and/or the value of the at least one other parameter known to be associated with the neurodegenerative disease, preferably Alzheimer's disease, further determined in step a1) or in step a'1), as defined in the section "Measurement of other known markers of neurodegenerative disease" above, in an iterative or genetic algorithm.

As used herein, the term "iterative algorithm" refers to a mathematical procedure that generates a sequence of improving approximate solutions for a class of problems. Starting from the choice of an initial score considered as a first draft solution, the algorithm proceeds by iterations during which it determines a succession of refined approximate solutions which get gradually closer to the searched solution.

Typically, the following algorithms may be used, when the virtual value V is obtained by summing the levels of at least two catecholamines measured in step a1), and when the level of at least one other marker of said neurodegenerative disease, preferably Alzheimer's disease, and/or the level of at least one other compound known to be associated with said neurodegenerative disease, preferably Alzheimer's disease, and/or the value of at least one other parameter known to be associated with said neurodegenerative disease, preferably Alzheimer's disease, are further determined in step a1):

$$\frac{V}{k_1 \times M_1} = score1$$

$$\frac{k \times V}{k_2 \times M_2} = score2$$

$$\frac{k' \times V}{k_3 \times M_3} = score3$$

$$\frac{k'' \times V}{k_4 \times M_4} = score4 \ldots$$

wherein

V is the sum of the levels of at least two catecholamines measured in step a1), preferably the sum of the levels of dopamine, adrenaline and noradrenaline measured in step a1), k, k', k", $k_1$, $k_2$ and $k_4$, identical or different, are coefficient different from 0, $M_1$, $M_2$, $M_3$ and $M_4$, are the levels of other markers of said neurodegenerative disease, preferably Alzheimer's disease, and/or of other compounds known to be associated with said neurodegenerative disease, preferably Alzheimer's disease, and/or the values of other parameters known to be associated with said neurodegenerative disease, preferably Alzheimer's disease, further determined in step a1). For example, $M_1$, $M_2$, $M_3$ and $M_4$ may respectively represent the age of the patient, the level of Aβ1-42, the level of phosphorylated tau and the level of ubiquitin.

The following iterative algorithm may also be used, when the virtual value V is obtained by summing the levels of dopamine, adrenaline and noradrenaline measured in step a1), and when the level of Aβ1-42 and the age of the patient are further determined in step a1):

$$\frac{V}{k_1 \times [A\beta 1 - 42]} = score1$$

$$\frac{score1}{age} = score2,$$

wherein

V is the sum of the levels of dopamine, adrenaline and noradrenaline measured in step a1), $k_1$ is a coefficient different from 0,

[Aβ1-42] is the level of Aβ1-42 determined in step a1), and

Age is the age of the patient.

As used herein, the term "genetic algorithm" refers to a search heuristic that mimics the process of natural evolution. Genetic algorithms belong to the larger class of evolutionary algorithms, which generate solutions to optimization problems using techniques inspired by natural evolution, such as inheritance, mutation, selection, and crossover. As known from the skilled person, in a genetic algorithm, a population of strings, which encode candidate solutions to an optimization problem, is evolved toward better solutions. Traditionally, solutions are represented in binary as strings of 0s and 1s, but other encodings are also possible. The evolution usually starts from a population of randomly generated individuals and happens in generations. In each generation, the fitness of every individual in the population is evaluated, multiple individuals are stochastically selected from the current population, and modified to form a new population. The new population is then used in the next iteration of the algorithm. Commonly, the algorithm terminates when either a maximum number of generations has been produced, or a satisfactory fitness level has been reached for the population.

When the level of at least one other known marker of said neurodegenerative disease, preferably Alzheimer's disease, and/or at least one other compound known to be associated with said neurodegenerative disease, preferably Alzheimer's disease, is further measured in the sample of biological fluid from said subject in step a1) or in step a'1), combining the levels measured in step a1) can mean more particularly applying the following algorithm:

$$R = k_c \times \frac{[M]}{([i] + [ii] + [iii])} - n$$

wherein $k_c$ is a constant, n is another constant, [x] is the respective level of one of the above defined catecholamines, x being i, ii or iii and [M] is the level of the at least one other known marker of said neurodegenerative disease, preferably Alzheimer's disease, and/or the at least one other compound known to be associated with said neurodegenerative disease, preferably Alzheimer's disease. Preferably, [M] is the level of Aβ1-42, more preferably the concentration of Aβ1-42.

As known from the skilled person, the constants $k_c$ and n may be empirically chosen from a cohort of patients including patients suffering from Alzheimer's disease and non-demented patients in such a way that it enables discriminating easily patients suffering from Alzheimer's disease from non-demented patients.

In a preferred embodiment, in particular when [M] is the concentration of Aβ1-42, $k_c$ is equal to 7,000. Such a value was empirically determined by the inventors in order to graphically focus the value R around zero. In still a preferred embodiment, in particular when [M] is the concentration of Aβ1-42, and more particularly when $k_c$ is equal to 7,000, n is equal to 1. Such a value was empirically determined by the inventors in order to obtain a predetermined value equal to 0.

The present inventors demonstrated that it was possible, using the method of the invention, to identify as non-demented, patients that were classified as AD patients. Such patients were therefore supposed to be false negative. This was in particular achieved by successively determining (i) the sum of the levels of dopamine, adrenaline and noradrenaline and (ii) the above defined combination of the level of Aβ1-42 and of the levels of dopamine, adrenaline and noradrenaline. Using these successive combinations, the discriminating power of the method of invention raised to 98.5%, with a specificity of 100% and a sensitivity of 96.5%.

Additionally, the above defined algorithm is in particular very useful in that it enables using a predetermined value equal to 0, thereby allowing the easy discrimination between patients suffering from Alzheimer's disease and patients not suffering from Alzheimer's disease.

Step of Comparison to a Predetermined Value

In a preferred embodiment of the invention, the method of diagnosis according to the invention further comprises a step a3) of comparing the virtual value determined in step a2) or the score determined in step a2b) with a predetermined value. In an alternative preferred embodiment of the invention, the method of diagnosis according to the invention further comprises a step a'2) of comparing the global level measured in step a'1) with a predetermined value.

The predetermined value may be a threshold value such as a median or mean or a range of values such as a confidence interval. Preferably, the predetermined value according to the invention corresponds to the threshold value enabling obtaining a diagnosis with the best specificity and the best sensitivity. Said predetermined value corresponds typically to the threshold value, determined using a population comprising a specific number of patients known not to suffer from a neurodegenerative disease, preferably from Alzheimer's disease, and a specific number of patients known to suffer from a neurodegenerative disease, preferably from Alzheimer's disease, which enables distinguishing patients not suffering from and patients suffering from a neurodegenerative disease, preferably Alzheimer's disease, with the best specificity and the best sensitivity. Preferably, the predetermined value is directly proportional to the catecholamines concentration enabling discriminating a pathological state from a non-pathological state in a given subject.

Typically, when step a1) of the method of the invention consists in measuring the levels of each of, preferably derivatized, dopamine, adrenaline and noradrenaline, in particular the levels of each of dopamine, adrenaline and noradrenaline derivatized with a fluorophore comprising a reactive NHS moiety, preferably with Fluoprobe®, Alexa Fluor® 488 or FAM X-SE, or with a fluorophore comprising a reactive isothiocyanate-type moiety, preferably with FITC or 5-FITC, using CZE-LIF, the electrophoretic separation being preferably performed in 25 min by applying preferably a 30 kV tension in the presence of a borate pH 9 buffer, IS (Ionic Strength) 40 mM, during 10 min at a temperature of preferably 25° C., the biological sample being preferably kept at a temperature of about 4° C. to 8° C. and the catecholamines being detected after an electrophoretic running time of preferably 17 to 20 min after a 40 cm migration inside the capillary using LIF with an argon-type laser with preferably a 3.5 mW power and an excitation wave length of 488 nm, the fluorescence being preferably collected with a 520 nm bandpass filter, and when step a2) consists in summing the levels of dopamine, adrenaline and noradrenaline measured in step a1), the predetermined value is preferably 200,000 $min^{-1}$.

As known by the skilled person, the predetermined value is dependent on the biological sample type, on the method used for measuring the level of the markers in the biological sample and on the algorithms used for combining these levels and obtaining the virtual value or the score. Thus, the predetermined value is preferably provided by using the same assay technique as used for measurement of the subject's marker levels, and by using the same algorithm as used for determining the virtual value or the score from the levels measured in the sample of biological fluid from the subject, to avoid any error in standardization.

Preferably, in the methods of the invention, it is further determined whether the virtual value determined in step a2) or the score determined in step a2b), or whether the global level measured in step a'1), is higher or lower than the predetermined value.

Preferably, when the virtual value or the score is higher than the predetermined value, or when the global level is higher than the predetermined value, it is significantly higher than the predetermined value.

Preferably, when the virtual value or the score is lower than the predetermined value, or when the global level is lower than the predetermined value, it is significantly lower than the predetermined value.

Typically, a virtual value obtained by summing the levels of dopamine, adrenaline and noradrenaline which is lower than the predetermined value is indicative of Alzheimer's disease. Alternatively, typically, a global level of dopamine, adrenaline and noradrenaline which is lower than the predetermined value is indicative of Alzheimer's disease.

Method for Therapeutic Follow-Up

Since, as shown by the inventors, an association or combination of the levels of catecholamines is indicative of Alzheimer's disease, quantifying catecholamines is also useful for following-up a treatment against Alzheimer's disease.

Therefore, the present invention also relates to a method for the therapeutic follow-up of a treatment against a neurodegenerative disease, preferably Alzheimer's disease, of a subject, comprising the steps of:

a1) measuring the level of each of at least two catecholamines in a sample of biological fluid from said subject before the treatment;

a2) determining a first virtual value by combining the levels measured in step a1), preferably applying one of the following algorithms:

$$V = \frac{[i]}{([i]+[ii]+[iii])}; V = \frac{[i]}{([ii]+[iii])}; V = \frac{[ii]}{([i]+[ii]+[iii])};$$

$$V = \frac{[ii]}{([i]+[iii])}; V = \frac{[iii]}{([i]+[ii]+[iii])}; V = \frac{[iii]}{([i]+[ii])};$$

$$V = \frac{([i]+[ii])}{([i]+[ii]+[iii])}; V = \frac{([i]+[ii])}{([ii]+[iii])}; V = \frac{([i]+[ii])}{([i]+[iii])};$$

$$V = \frac{([i]+[ii])}{[iii]}; V = \frac{([i]+[iii])}{([i]+[ii]+[iii])}; V = \frac{([i]+[iii])}{([ii]+[iii])};$$

$$V = \frac{([i]+[iii])}{([ii]+[i])}; V = \frac{([i]+[iii])}{[ii]}; V = \frac{([ii]+[iii])}{([i]+[ii]+[iii])};$$

$$V = \frac{([ii]+[iii])}{([i]+[iii])}; V = \frac{([ii]+[iii])}{([i]+[ii])}; V = \frac{([ii]+[iii])}{[i]}; \text{ or}$$

$$V = [i]+[ii]+[iii];$$

wherein V is the virtual value to be determined and [x] is the respective level of one of said catecholamines, x being i, ii or iii;

b1) measuring the level of each of said at least two catecholamines in a sample of biological fluid from said subject during or after the treatment;

b2) determining a second virtual value by combining the levels measured in step b1), preferably applying one of the following algorithms:

$$V = \frac{[i]}{([i]+[ii]+[iii])}; V = \frac{[i]}{([ii]+[iii])}; V = \frac{[ii]}{([i]+[ii]+[iii])};$$

$$V = \frac{[ii]}{([i]+[iii])}; V = \frac{[iii]}{([i]+[ii]+[iii])}; V = \frac{[iii]}{([i]+[ii])};$$

$$V = \frac{([i]+[ii])}{([i]+[ii]+[iii])}; V = \frac{([i]+[ii])}{([ii]+[iii])}; V = \frac{([i]+[ii])}{([i]+[iii])};$$

$$V = \frac{([i]+[ii])}{[iii]}; V = \frac{([i]+[iii])}{([i]+[ii]+[iii])}; V = \frac{([i]+[iii])}{([ii]+[iii])};$$

$$V = \frac{([i]+[iii])}{([ii]+[i])}; V = \frac{([i]+[iii])}{[ii]}; V = \frac{([ii]+[iii])}{([i]+[ii]+[iii])};$$

$$V = \frac{([ii] + [iii])}{([i] + [iii])}; V = \frac{([ii] + [iii])}{([i] + [ii])}; V = \frac{([ii] + [iii])}{[i]}; \text{ or}$$
$$V = [i] + [ii] + [iii];$$

wherein V is the virtual value to be determined and [x] is the respective level of one of said catecholamines, x being i, ii or iii; and c) based on the first and second virtual values respectively determined in steps a2) and b2), determining whether said subject benefits from said treatment against a neurodegenerative disease, preferably Alzheimer's disease;

or a') measuring a first global level of at least two catecholamines in a sample of biological fluid from said subject before the treatment;

b') measuring a second global level of said at least two catecholamines in a sample of biological fluid from said subject during or after the treatment; and c') based on the first and second global levels respectively determined in steps a') and b'), determining whether said subject benefits from said treatment against a neurodegenerative disease, preferably Alzheimer's disease.

As used herein, the term "neurodegenerative disease" has the same meaning as the one defined herein above in section "Diagnosis of a neurodegenerative disease". Preferably, said neurodegenerative disease is Alzheimer's disease.

As used herein, the term "treatment against a neurodegenerative disease" refers to any treatment useful in preventing, reducing and/or stopping the progression of said neurodegenerative disease.

Preferably, the steps a1) and b1) of measuring the level of each of at least two catecholamines, and the steps a') and b') of measuring the global level of at least two catecholamines, are carried out as defined herein above in section "Step of measuring the level of at least two catecholamines".

Preferably, in the method for therapeutic follow-up of the invention, the level of at least one other known marker of said neurodegenerative disease, preferably Alzheimer's disease, and/or of at least one other compound known to be associated with said neurodegenerative disease, preferably Alzheimer's disease, is further measured in the sample of biological fluid obtained from said subject and/or the value of at least one other parameter known to be associated with said neurodegenerative disease, preferably Alzheimer's disease, is further determined in said subject in steps a1) and b1) or in steps a') and b'), in particular as defined herein above in section "Measurement of other known markers of neurodegenerative disease".

Preferably, the steps a2) and b2) of determining a virtual value are carried out as defined herein above in section "Step of determining a virtual value".

Preferably, the method for therapeutic follow-up of the invention further comprise steps a2b) and b2b) or steps a'b) and b'b) of determining a score by combining respectively the virtual value determined in step a2) or b2) or the global level determined in step a') or b') and the level of said at least one other known marker of Alzheimer's disease and/or of said at least one other compound known to be associated with Alzheimer's disease and/or the value of said at least one other parameter known to be associated with Alzheimer's disease further determined in step a1) or b1) or in step a') or b'), in an iterative or genetic algorithm, as defined herein above in section "Step of determining a score".

Preferably, the method of therapeutic follow-up of the invention further comprises a step a3) and a step b3) of comparing the virtual values determined in steps a2) and b2) or the scores determined in steps a2b) and b2b) or in steps a'b) and b'b) with a predetermined value, in particular as defined herein above in section "Step of comparison to a predetermined value". Still preferably, the method of therapeutic follow-up of the invention further comprises a step a'2) and a step b'2) of comparing the global levels measured in steps a') and b') with a predetermined value, in particular as defined herein above in section "Step of comparison to a predetermined value".

In another preferred embodiment, the method of therapeutic follow-up of the invention further comprises a step pre-c) of comparing the first virtual value determined in step a2) or the first score determined in step a2b) with the second virtual value determined in step b2) or the second score determined in step b2b). In another preferred embodiment, the method of therapeutic follow-up of the invention further comprises a step pre-c') of comparing the first global level measured in step a') with the second global level measured in step b').

EXAMPLES

Example 1

The present example demonstrates that quantifying and combining the levels of dopamine, adrenaline and noradrenaline enables establishing a very specific and sensitive diagnosis of Alzheimer's disease.

Material and Methods

Collection and Storage of Cerebrospinal Fluids (CSF)

Every CSF sample analyzed in this study was collected from patients staying in the Neurology Department of the Ulm University (Germany) in 2008 and 2009. Collection and analysis of these samples were approved by the Ulm University ethics committee. Every patient gave written informed consent to their participation in the study and underwent clinical, neurological and neuroradiological examinations and neuropsychological examinations including the Mini-mental state examination (MMSE) in order to investigate global cognitive functioning. If cognitive deterioration had been suggested, a detailed psychometric test battery covering executive functions, memory, constructional abilities, premorbid verbal intelligence and depression was carried out in order to assess, characterize and diagnose the origin of these cognitive disorders (Steinacker et al. (2008) *Arch. Neurol.* 65:1481-1487).

CSF were aliquoted in the two hours following collection and stored at −80° C.

CSF Derivatization

The commercial fluorophore (in powder form) was diluted in a DMSO solution (99% pure) at a concentration of 10 mg/ml, aliquoted and stored at −20° C. 1 µl of the fluorophore solution was added to 24 µl of borate buffer (derivatization solution). A two-fold dilution was then performed on CSF by mixing 25 µl of CSF with 25 µl of the derivatization solution. For fluorophores comprising a reactive NHS moiety (N-hydroxysuccinimydil ester) such as Fluoprobe®, Alexa Fluor® 488 or FAM X-SE, the derivatization reaction was complete after a 5 minute-incubation at room temperature. For fluorophores comprising a reactive isothiocyanate-type moiety such as FITC or 5-FITC, the derivatization reaction was complete after a 12 hour-incubation at 8° C.

For use as standards, catecholamines which were stored in powder form at −20° C. were solubilized in a deionized water solution.

Capillary Electrophoresis Coupled to Laser-Induced Fluorescence (CE-LIF) Analysis Capillary Preparation Capillaries used were in fused silica and displayed a 50 μm-inner diameter and a 375 μm-outer diameter. They were 50 cm long for a total effective length of 40 cm. Each new capillary was pre-treated by applying a pressure of 138 kPa at the entry of the capillary enabling carrying out the following sequence: 0.1 M NaOH for 5 min, 1 M NaOH for 5 min and deionized water for 5 min. Every washing solution and electrolytes solution was filtered on filters displaying a 0.2 μm pore diameter. After this pre-treatment, a washing step based on deionized water and 0.1M NaOH rinsing was performed.

Capillary Equilibration Between Each Analysis

Between each analysis, the capillary was rinsed by applying a pressure of 138 kPa, and deionized water through the capillary for 5 min, followed by washing with a DMSO/water (50:50) solution for 2 min, and with diluted NaOH for 5 min. Finally, the capillary was conditioned by borate pH 9 separation buffer, IS 40 mM, and by applying a pressure of 138 kPa (in the normal direction).

Conditions for Sample Injection

Experiments were carried out using a Beckman Coulter PA 800 ProteomLab capillary electrophoresis coupled to LIF detection. Samples were introduced in the capillary by hydrodynamic injection under a pressure of 3.4 kPa. The capillary was heated at 25° C. and derivatized CSF samples were kept at 8° C. using the PA 800 sample storage module.

Analysis and Detection

Electrophoretic separation was performed in 25 min by applying a 30 kV tension in the presence of a borate pH 9 running buffer, IS 40 mM.

Detection of catecholamines was carried out after an electrophoretic running time of 17 to 20 min after a 40 cm migration inside the capillary. Detection was obtained by fluorescence emission of the fluorophore linked to catecholamines. Catecholamines were thus detected by laser-induced fluorescence (LIF) with an argon-type laser with a 3.5 mW power and an excitation wave-length of 488 nm, fluorescence emission being collected with a 520 nm band-pass filter.

Data Treatment and Assessment of the Diagnosis Criteria

Figure 1:
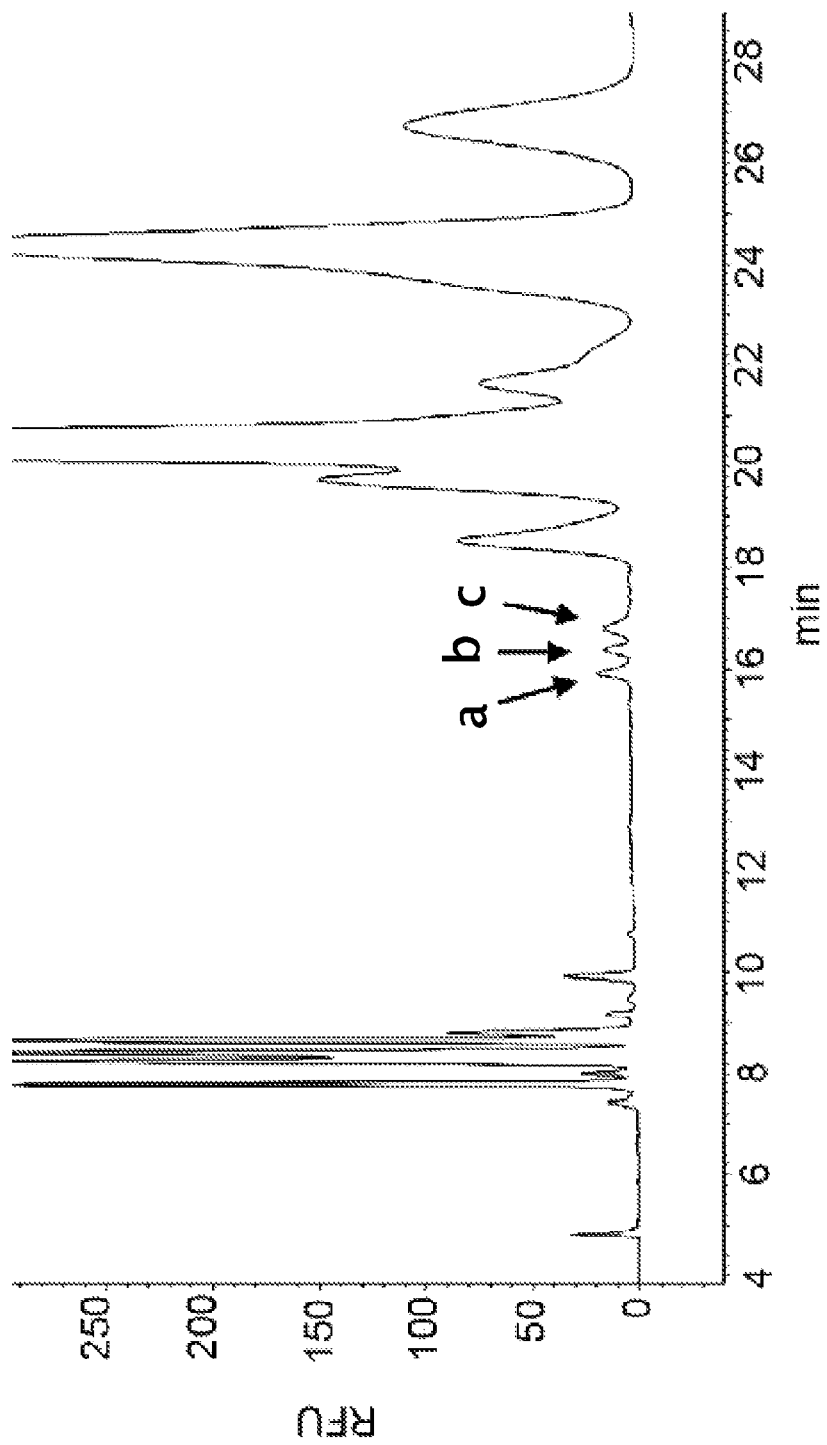
FIG. 1 shows the electrophoretic profile obtained from the analysis of a cerebrospinal fluid (CSF) sample derivatized by FluoProbe® as described in Example 1. The arrows show the peaks corresponding to catecholamines. a represents adrenaline; b noradrenaline and c dopamine.

FIG. 1 shows the electrophoretic profile obtained from the analysis of a CSF sample derivatized by Fluoprobe®.

Areas, corrected areas and peak height corresponding to catecholamines were determined using the 32 Karat software (Beckman Coulter). Combination of the information was made by summation or by a mathematical operation involving the association of at least two catecholamines.

Results

CZE-LIF enabled integrating the peak areas related to the concentrations of catecholamines (dopamine, adrenaline and noradrenaline) in 46 CSF samples obtained from patients suffering from Alzheimer's disease and non-demented patients. The results obtained from the 46 CSF samples were transferred on a diagram representing the distribution of the different analyzed CSF samples in abscissa and the virtual values obtained from the corrected areas of the catecholamines (in $min^{-1}$) in ordinate. Circles correspond to CSF samples of patients who were considered as non-demented patients by the conventional diagnostic test and squares correspond to CSF samples of patients who were considered as suffering from Alzheimer's disease by the conventional diagnostic test.

Figure 2:
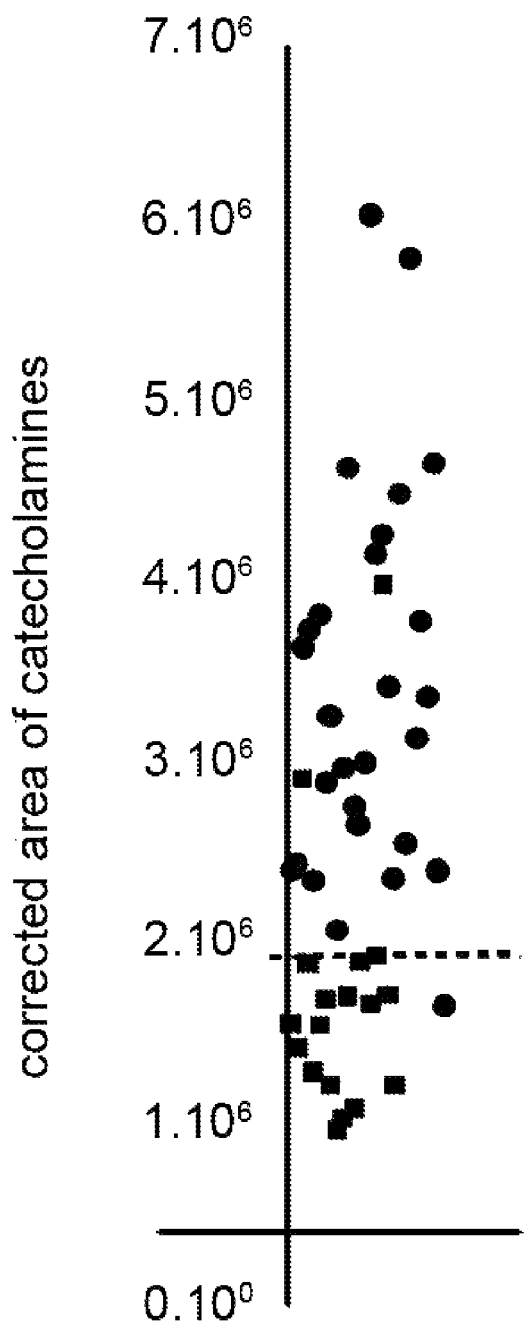
FIG. 2 shows a diagram representing in abscissa the distribution of the CSF samples analyzed in Example 1 obtained from non-demented patients, which are patients considered as not suffering from Alzheimer's disease by a conventional diagnostic test (circles) and patients considered as suffering from Alzheimer's disease by a conventional diagnostic test (squares), and the addition of corrected areas of the catecholamines (in $min^{-1}$) in ordinate.

Calculation of the simple addition of the corrected peak areas corresponding to catecholamines (i.e. the peak areas corresponding to catecholamines divided by the migration time of these compounds) (ΣAc(Cth)) revealed a net distribution between non-demented patients (circles) and patients suffering from Alzheimer's disease (squares), on either side of a threshold value, which was fixed at 200,000 $min^{-1}$ and which enabled obtaining the best diagnostic power (FIG. 2).

The discriminating power obtained by combining the three catecholamines dopamine, adrenaline and noradrenaline, had never been reported in the literature so far, according to the inventors' knowledge. Combining catecholamines by adding their areas (corrected by the running time) drastically increased the discriminating power which enabled reaching a diagnostic power (including sensitivity and specificity) superior to 90% (table 1).

TABLE 1

| Sensitivity and specificity of the method of the invention | | | |
| --- | --- | --- | --- |
| Clinical judgment | Specificity (%) | Sensitivity (%) | Power (%) |
| Combination of 3 catecholamines | 96.4 | 89 | 93 |

Advantages of the Method of the Invention

The method according to the invention is routinely applicable, at a low cost.

Indeed, resolutions obtained for the electrophoretic separation of catecholamines (≥1.5) are compatible with a quantitative method (FIG. 1). Repeatability (relative standard deviation, RSD) of peak areas was less than 5% and RSD of running time was less than 2%.

Furthermore, the total time for analyzing the sample (including conditioning with separation buffer and capillary equilibration) was only 48 min. The method according to the invention thus enables reaching high scale. Furthermore, parallelization is possible by miniaturizing the method or using multi-capillaries electrophoresis.

Advantageously, a very small amount of CSF sample (25 μl) is necessary to implement the method according to the invention. A very high number of analyses can be performed with this low volume, for one single sample.

The analysis described in the present invention is moreover automated. Indeed, the PA 800 capillary electrophoresis is totally automated and enables programming sequences for samples analyses over several days without any exterior intervention, therefore minimizing operators intervention and cost. Using the above described method, the inventors estimated that 30 CSF samples could be analyzed over 24 hours.

Finally, the cost of the analysis is very low. Indeed, using 310 mg of borate buffer, 10 ml of water, 200 mg of sodium hydroxide, 750 μl of DMSO (99%), 10 μg of fluorophore and 55 cm of fused silica capillary, corresponds to a cost of about 5 €.

Example 2

This example demonstrates that quantifying and combining the levels of dopamine, adrenaline and noradrenaline and of Aβ1-42 enables improving further the specificity and sensitivity of the method of diagnosis of Alzheimer's disease.

Material and Methods

Patients

The patients studied were the same as the ones studied in Example 1.

Measurement of the Catecholamines Levels

The levels of catecholamines were measured as shown in Example 1.

Aβ1-42 Assay and Measurement

The concentration of Aβ1-42 in CSF was measured using a sandwich ELISA obtained from Innogenetics, Belgium. The assay detection limit was 50 pg/ml, with a linearity in the range of 200 pg/ml to 1500 pg/ml. For the statistical analysis, a comparison of the Aβ1-42 distribution between subgroups in the study population was based on nonparametric rank tests (for two groups, Wilcoxon-Mann-Witney U-test).

Results

As a first step, the summation of corrected peak areas corresponding to catecholamines was performed as described in Example 1.

Figure 3:
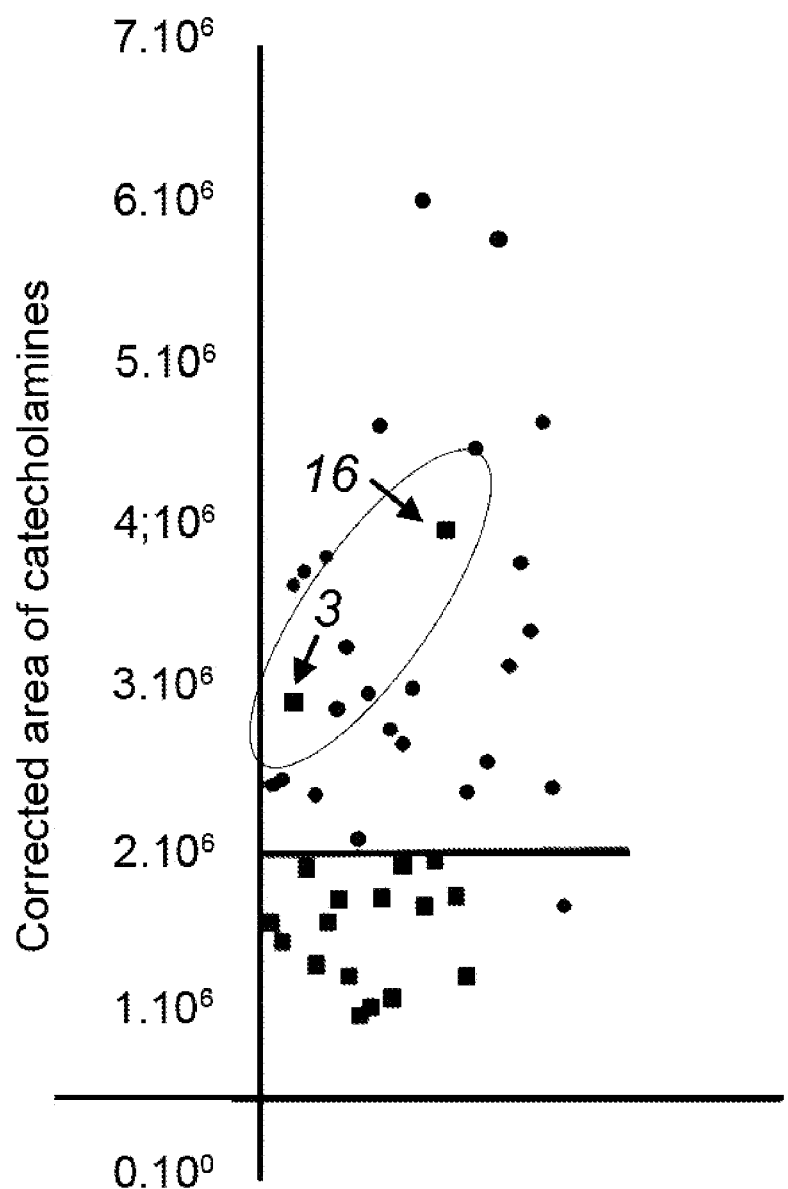
FIG. 3 shows the same diagram that FIG. 2 but wherein patients no 3 and no 16 are indicated by arrows.

The distribution of the respective corrected peak areas from CSF of the 46 patients suffering from Alzheimer's disease (AD) or non-demented (nAD) was reported on a single graphic (FIG. 3) which enabled classifying patients AD vs nD.

In a concomitant way, a R ratio was calculated according to the following equation:

$$R = \frac{7000 \times [A\beta 1 - 42]}{\sum Ac(Cath)} - 1.$$

Figure 4:
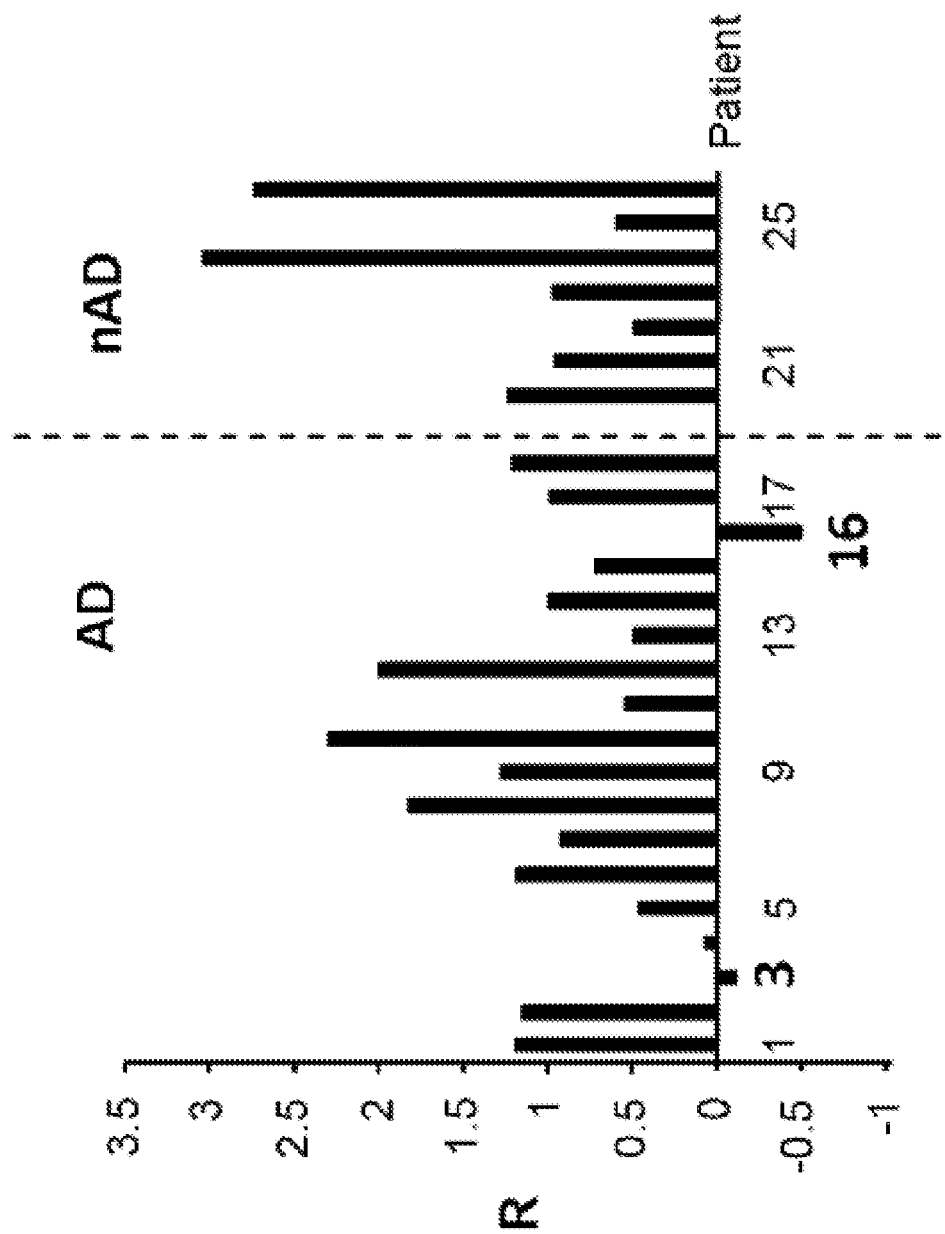
FIG. 4 shows histograms representing the virtual value (R) obtained in 26 subjects by applying the following algorithm.

The constants of this equation were fixed in such a way that the threshold value was situated graphically around zero, thereby enabling easily distinguishing subgroups of patients (FIG. 4).

As illustrated in FIG. 4, the group of patients identified as suffering from Alzheimer's disease using conventional diagnostic tests actually included two false positive cases (patients 3 and 16).

Therefore, in view of this additional analysis, patients 3 and 16 could be either considered as patients suffering from AD or excluded from the test, in order to determine the discriminating power of the method of the invention.

In both cases the specificity and the sensitivity of the test were increased from 96.4% to 100% and from 89% to 96.5% respectively (table 2).

TABLE 2

Sensitivity and specificity of the method of the invention

| Clinical judgment | Specificity (%) | Sensitivity (%) | Power (%) |
|---|---|---|---|
| Combination of 3 catecholamines and Aβ1-42 | 100 | 96.5 | 98.5 |

Example 3

This example demonstrates that the discrimination power of the method of the invention can be increased by combining the levels of catecholamines and other parameters known to be associated with Alzheimer's disease.

Material and Methods

Patients

The patients studied were the same as the ones studied in Example 1. Their age was determined.

Measurement of the Catecholamines Levels

The levels of catecholamines were measured as shown in Example 1.

Algorithms Used

Two algorithms were used to combine the above-parameters. First, the levels of catecholamines was summed are described in Example 1, without including the age of the patients. The results of the use of this algorithm are shown on FIG. 5B. Secondly, the levels of catecholamines was summed as described in Example 1, then divided by the age of the patient. The results of the use of this algorithm are shown on FIG. 5A.

Results

The comparison between FIGS. 5A and 5B shows the impact of including the age of the patients as an additional parameter in the algorithms used in the methods of the invention. Using this algorithm, the inventors observed an increase in the discrimination power between non-dement patients and patients suffering from Alzheimer's disease.

Example 4

This example also demonstrates that the discrimination power of the method of the invention can be increased by combining the levels of catecholamines and other parameters known to be associated with Alzheimer's disease.

Material and Methods

Patients

The patients studied were the same as the ones studied in Example 1. Their age was determined.

Measurement of the Catecholamines Levels

The levels of catecholamines were measured as shown in Example 1.

Measurement of the level of Aβ1-42

The levels of Aβ1-42 were measured as shown in Example 2.

Algorithms Used

Two algorithms were used to combine the above-parameters. First, the levels of catecholamines was summed are described in Example 1, without including the age of the patients or the levels of Aβ1-42. Secondly, the levels of catecholamines was summed as described in Example 1, and used in the following algorithm:

$$score1 = \sum Ac(Cath)$$

$$score2 = \frac{\sum Ac(Cath)}{age}$$

$$score3 = \frac{K1 \times [A\beta 1 - 42]}{\sum Ac(Cath)}$$

wherein K1 is a constant equal to 7,000, [Aβ1-42] represents the concentration of Aβ1-42 and ΣAc(Cath) represents the sum of the corrected areas corresponding to adrenaline, noradrenaline and dopamine.

Results

The inventors demonstrated the impact of including the age of the patients and the level of Aβ1-42 as additional parameters in the algorithms used in the methods of the invention. Using this algorithm, the inventors observed an increase in the discrimination power between non-dement patients and patients suffering from Alzheimer's disease. Indeed, the discrimination power then reached 100% in terms of both specificity and sensitivity.

Example 5

This example still demonstrates that the discrimination power of the method of the invention can be increased by combining the levels of catecholamines and other parameters known to be associated with Alzheimer's disease.
Material and Methods
Patients The patients studied were the same as the ones studied in Example 1. Their age was determined.
Measurement of the Catecholamines Levels The levels of catecholamines were measured as shown in Example 1.
Measurement of the level of Aβ1-42

The levels of Aβ1-42 were measured as shown in Example 2.
Measurement of the Total Tau Level CSF was collected in polypropylene tubes on ice in 0.5 ml aliquots. In case of contamination with blood due to the procedure, the sanguineous CSF was collected in a separate tube. For scientific purposes, only clear CSF was used. For this study, a total of 1 ml was taken. Aliquots were centrifuged at 4° C. at 10.000×g for 10 min and stored at −80° C. until analysis. p-tau was measured by a developed enzyme-linked immunosorbent assay (ELISA). Tau-protein was measured in duplicate by an enzyme linked immunosorbent-assay (ELISA), which recognizes unphosphorylated and normally phosphorylated tau-protein. Hyperphosphorylated tau-protein was not recognized by this assay (Innotest hTAU, Innogenetics, Zwijndecht, Belgium). For total tau, the inventors used a commercially available ELISA (Innogenetics, Belgium).
Algorithms Used The levels of catecholamines were summed as described in Example 1, then the following algorithm was applied:

$$score1 = \sum Ac(Cath)$$

$$score2 = \frac{\sum Ac(Cath)}{age}$$

$$score3 = \frac{K1 \times [A\beta1-42]}{\sum Ac(Cath)}$$

$$score4 = \frac{K2 \times [Tau]}{\sum Ac(Cath)}$$

wherein K1 is a constant equal to 7,000, [Aβ1-42] represents the concentration of Aβ1-42, K2 is a constant equal to 15,000, [Tau] represents the concentration of Tau, and ΣAc(Cath) represents the sum of the corrected areas corresponding to adrenaline, noradrenaline and dopamine.

Score 1, score 2, score 3 and score 4 were calculated using iterative algorithm or in the same time in a genetic algorithm context; in order to exclude positive or negative false to increase the discrimination power of the test.

The results of the use of this algorithm are shown on FIG. 6.
Results

FIG. 6 shows the impact of including the age of the patients, the level of Aβ1-42 and the total Tau level as additional parameters in the algorithms used in the methods of the invention. Using this algorithm, the inventors observed an almost complete discrimination between non-dement patients and patients suffering from Alzheimer's disease.

Example 6

This example demonstrates the discrimination power of the method of the invention between Alzheimer's disease and other neurological diseases.
Materials and Methods
Patients 66 "blinded" samples were analyzed: samples from 10 patients suffering from amyloidose lateral sclerosis (ALS), from 15 non dement controls (nD), from 10 patients suffering from Alzheimer's disease (AD), from 11 patients suffering from Parkinson's disease (PD), from 10 patients suffering from Parkinson's dementia (PDD) and from 5 patients suffering from Creutzfeldt-Jakob disease (CJD).
Analysis of the Samples The samples were analyzed consecutively. Every sample was analyzed twice.

The levels of catecholamines were measured as shown in Example 1.

The level of ubiquitin was measured using the same method.

For each sample, the virtual value was calculated based on the peaks areas given by the three considered catecholamines: the difference obtained for the determination of two replicates never exceeded 10%.

The data shown in FIG. 7 are the average level of summed catecholamines from 2 successive analyses performed for each sample.
Results As shown in FIG. 7, the average level of summed catecholamines is much lower when the patients suffer from AD compared to the non-dement controls (nD). On the contrary, the catecholamines virtual value from patients suffering from PD or ALS was not significantly different from the nD patients.

These results thus demonstrate the capacity of the method of the invention to discriminate AD from nD but also AD from PD or from ALS.

In addition, the inventors demonstrated that, in the capillary electrophoretic profile (FIG. 8), one early peak corresponded to ubiquitin and could be measured simultaneously to catecholamine analysis. This led to the opportunity to include the ubiquitin level in the algorithm to further increase the determination power.

Accordingly, if the level of summed catecholamines was bellow 1,250,000, which corresponds to the cut off value identified between AD and nD patient, the ubiquitin level in the CSF samples was measured.

As shown in FIG. 9, determining the level of ubiquitin in these samples, first discriminated on the basis of the sum of the levels of catecholamines, enabled significantly distinguishing AD from PDD.

The invention claimed is:
1. An in vitro method for diagnosing subjects with Alzheimer's disease or Parkinson disease with dementia among subjects suffering from dementia selected from the group consisting of Alzheimer's disease, Parkinson disease, Parkinson disease with dementia, amyotrophic lateral sclerosis, and Creutzfeldt-Jacob's disease, said method compris- ing the steps of selecting exclusively dopamine, adrenaline and noradrenaline in a sample of biological fluid from said subject and of
- a1) incubating said dopamine, adrenaline and noradrenaline in said sample with 3,6-diamino-9-[2,4(or 2,5)-dicarboxyphenyl]-4,5-disulfoxanthylium inner salt lithium salt (1:3);
- a2) measuring separately the molar concentration of each of said dopamine, adrenaline and noradrenaline derivatized with 3,6-diamino-9-[2,4(or 2,5)-dicarboxyphenyl]-4,5-disulfoxanthylium inner salt lithium salt (1:3);
- a3) determining a virtual value by combining the levels measured in step a2) applying one of the following algorithms:

$$V = \frac{[i]}{([i]+[ii]+[iii])}; V = \frac{[i]}{([ii]+[iii])}; V = \frac{[ii]}{([i]+[ii]+[iii])};$$

$$V = \frac{[ii]}{([i]+[iii])}; V = \frac{[iii]}{([i]+[ii]+[iii])}; V = \frac{[iii]}{([i]+[ii])};$$

$$V = \frac{([i]+[ii])}{([i]+[ii]+[iii])}; V = \frac{([i]+[ii])}{([ii]+[iii])}; V = \frac{([i]+[ii])}{([i]+[iii])};$$

$$V = \frac{([i]+[ii])}{[iii]}; V = \frac{([i]+[iii])}{([i]+[ii]+[iii])}; V = \frac{([i]+[iii])}{([ii]+[iii])};$$

$$V = \frac{([i]+[iii])}{([ii]+[i])}; V = \frac{([i]+[iii])}{[ii]}; V = \frac{([ii]+[iii])}{([i]+[ii]+[iii])};$$

$$V = \frac{([ii]+[iii])}{([i]+[iii])}; V = \frac{([ii]+[iii])}{([i]+[ii])}; V = \frac{([ii]+[iii])}{[i]}; \text{ or}$$

$$V = [i]+[ii]+[iii];$$

wherein V is the virtual value to be determined and [i] is the level of said dopamine, [ii] is the level of said adrenaline and [iii] is the level of said noradrenaline; and
- a4) comparing the virtual value determined in step a3) with a threshold value based on a number of healthy patients, a number of patients suffering from Alzheimer's disease and a number of patients suffering from Parkinson disease with dementia, using the same algorithm as used for determining the virtual value in step a3); and
- b) determining whether said subject suffers from Alzheimer's disease or Parkinson disease with dementia when the virtual value determined in step a3) is lower than said threshold value.

2. The method according to claim 1, wherein the virtual value is determined in step a3) by summing the levels of dopamine, adrenaline and noradrenaline measured in step a2).

3. The method according to claim 1, wherein said sample of biological fluid is selected from the group consisting of cerebrospinal fluid, serum, plasma, urine and saliva sample.

4. The method according to claim 1, wherein measuring the level of dopamine, adrenaline and noradrenaline in step a2) is performed by capillary electrophoresis.

5. The method according to claim 4, wherein measuring the level of each of dopamine, adrenaline and noradrenaline in step a2) is performed by capillary electrophoresis coupled to laser-induced fluorescence.

6. A method for the therapeutic follow-up of a treatment against Alzheimer's disease or Parkinson disease with dementia of a subject, wherein said subject suffers from dementia selected from the group consisting of Alzheimer's disease, Parkinson disease, Parkinson disease with dementia, amyotrophic lateral sclerosis, and Creutzfeldt-Jacob's disease, said method comprising the steps of selecting exclusively dopamine, adrenaline and noradrenaline in a sample of biological fluid from said subject and of
- a1) incubating said dopamine, adrenaline and noradrenaline in said sample with 3,6-diamino-9-[2,4(or 2,5)-dicarboxyphenyl]-4,5-disulfoxanthylium inner salt lithium salt (1:3);
- a2) measuring separately the molar concentration of each of said dopamine, adrenaline and noradrenaline before the treatment, said dopamine, adrenaline, and noradrenaline each derivatized with 3,6-diamino-9-[2,4(or 2,5)-dicarboxyphenyl]-4,5-disulfoxanthylium inner salt lithium salt (1:3);
- a3) determining a first virtual value by combining the levels measured in step a2) applying one of the following algorithms:

$$V = \frac{[i]}{([i]+[ii]+[iii])}; V = \frac{[i]}{([ii]+[iii])}; V = \frac{[ii]}{([i]+[ii]+[iii])};$$

$$V = \frac{[ii]}{([i]+[iii])}; V = \frac{[iii]}{([i]+[ii]+[iii])}; V = \frac{[iii]}{([i]+[ii])};$$

$$V = \frac{([i]+[ii])}{([i]+[ii]+[iii])}; V = \frac{([i]+[ii])}{([ii]+[iii])}; V = \frac{([i]+[ii])}{([i]+[iii])};$$

$$V = \frac{([i]+[ii])}{[iii]}; V = \frac{([i]+[iii])}{([i]+[ii]+[iii])}; V = \frac{([i]+[iii])}{([ii]+[iii])};$$

$$V = \frac{([i]+[iii])}{([ii]+[i])}; V = \frac{([i]+[iii])}{[ii]}; V = \frac{([ii]+[iii])}{([i]+[ii]+[iii])};$$

$$V = \frac{([ii]+[iii])}{([i]+[iii])}; V = \frac{([ii]+[iii])}{([i]+[ii])}; V = \frac{([ii]+[iii])}{[i]}; \text{ or}$$

$$V = [i]+[ii]+[iii];$$

wherein V is the virtual value to be determined and [i] is the level of said dopamine, [ii] is the level of said adrenaline and [iii] is the level of said noradrenaline;
- b1) measuring separately the molar concentration of each of said dopamine, adrenaline and noradrenaline derivatized with 3,6-diamino-9-[2,4(or 2,5)-dicarboxyphenyl]-4,5-disulfoxanthylium inner salt lithium salt (1:3) during or after the treatment;
- b2) determining a second virtual value by combining the levels measured in step b1) applying one of the following algorithms:

$$V = \frac{[i]}{([i]+[ii]+[iii])}; V = \frac{[i]}{([ii]+[iii])}; V = \frac{[ii]}{([i]+[ii]+[iii])};$$

$$V = \frac{[ii]}{([i]+[iii])}; V = \frac{[iii]}{([i]+[ii]+[iii])}; V = \frac{[iii]}{([i]+[ii])};$$

$$V = \frac{([i]+[ii])}{([i]+[ii]+[iii])}; V = \frac{([i]+[ii])}{([ii]+[iii])}; V = \frac{([i]+[ii])}{([i]+[iii])};$$

$$V = \frac{([i]+[ii])}{[iii]}; V = \frac{([i]+[iii])}{([i]+[ii]+[iii])}; V = \frac{([i]+[iii])}{([ii]+[iii])};$$

$$V = \frac{([i]+[iii])}{([ii]+[i])}; V = \frac{([i]+[iii])}{[ii]}; V = \frac{([ii]+[iii])}{([i]+[ii]+[iii])};$$

$$V = \frac{([ii]+[iii])}{([i]+[iii])}; V = \frac{([ii]+[iii])}{([i]+[ii])}; V = \frac{([ii]+[iii])}{[i]}; \text{ or}$$

$$V = [i]+[ii]+[iii];$$

wherein V is the virtual value to be determined and [i] is the level of said dopamine, [ii] is the level of said adrenaline and [iii] is the level of said noradrenaline; and c) based on the first and second virtual values respectively determined in steps a3) and b2), determining whether said subject benefits from said treatment against Alzheimer's disease or Parkinson disease with dementia.

\* \* \* \* \*